(12) United States Patent
Vojnovic et al.

(10) Patent No.: US 9,212,985 B2
(45) Date of Patent: Dec. 15, 2015

(54) DETECTING OBJECTS

(75) Inventors: Borivoj Vojnovic, Oxford (GB); Paul Richard Barber, Oxford (GB); Iestyn Pope, Cardiff (GB); Paul James Smith, Cardiff (GB); Rachel Jane Errington, Cardiff (GB)

(73) Assignee: ISIS INNOVATION LIMITED, Oxford (GB)

( * ) Notice: Subject to any disclaimer, the term of this patent is extended or adjusted under 35 U.S.C. 154(b) by 1142 days.

(21) Appl. No.: 12/523,878

(22) PCT Filed: Jan. 22, 2008

(86) PCT No.: PCT/GB2008/000216
§ 371 (c)(1),
(2), (4) Date: Feb. 11, 2011

(87) PCT Pub. No.: WO2008/090330
PCT Pub. Date: Jul. 31, 2008

(65) Prior Publication Data
US 2011/0136165 A1    Jun. 9, 2011

(30) Foreign Application Priority Data

Jan. 22, 2007    (GB) .................................. 0701201.6

(51) Int. Cl.
| | |
|---|---|
| *C12M 1/34* | (2006.01) |
| *C12Q 1/06* | (2006.01) |
| *C12Q 1/02* | (2006.01) |
| *G01N 15/14* | (2006.01) |

(Continued)

(52) U.S. Cl.
CPC ........ *G01N 15/1456* (2013.01); *G01N 15/1434* (2013.01); *G03H 2001/0033* (2013.01); *G03H 2001/0447* (2013.01); *G03H 2001/0825* (2013.01)

(58) Field of Classification Search
CPC .......... G01N 15/1456; G01N 15/1434; G03H 2001/0825; G03H 2001/0447; G03H 2001/0033
USPC ........................................... 435/29, 39, 288.7
See application file for complete search history.

(56) References Cited

U.S. PATENT DOCUMENTS 4,555,633 A * 11/1985 Bjorkelund .............. 250/559.15
5,249,077 A    9/1993 Laronga et al.

(Continued)

FOREIGN PATENT DOCUMENTS

| CA | 1195426 | 10/1985 | |
|---|---|---|---|
| WO | WO 94/13835 | * 6/1994 | ............... C12Q 1/68 |
| WO | WO-03/060446 | 7/2003 | |

OTHER PUBLICATIONS

Examination Report for EP Application No. 08 701 890.9, Oct. 12, 2011, European Patent Office, Rijswijk, Netherlands.

(Continued)

*Primary Examiner* — William H Beisner
*Assistant Examiner* — Danielle Henkel
(74) *Attorney, Agent, or Firm* — Marvin Petry; Stites & Harbison PLLC

(57) ABSTRACT

The invention provides apparatus and methods for detecting objects in samples. The sample is held in the transmission path of light from a light source to a detector, whereby light from the light source interacts with objects in the sample. The patterns of light incident on the detector subsequent to its interaction with the objects are directly used to determine the presence of objects in the sample.

32 Claims, 22 Drawing Sheets

(51) Int. Cl.
*G03H 1/00* (2006.01)
*G03H 1/04* (2006.01)
*G03H 1/08* (2006.01)

(56) References Cited

U.S. PATENT DOCUMENTS

| | | | |
|---|---|---|---|
| 6,411,406 | B1 | 6/2002 | Kreuzer |
| 6,678,391 | B2 | 1/2004 | Yahiro |
| 6,707,958 | B2 | 3/2004 | Pering et al. |
| 6,876,474 | B2 | 4/2005 | Kreuzer et al. |
| 7,008,794 | B2 * | 3/2006 | Goh et al. ............ 436/164 |
| 7,016,523 | B1 * | 3/2006 | Ogawa ............ 382/133 |
| 7,019,834 | B2 | 3/2006 | Sebok et al. |
| 7,295,310 | B2 | 11/2007 | Nieuwenhuis et al. |
| 2003/0147552 | A1 | 8/2003 | Foran et al. |
| 2004/0174523 | A1 | 9/2004 | Uhl et al. |
| 2005/0105077 | A1 | 5/2005 | Padmanabhan et al. |
| 2005/0190286 | A1 * | 9/2005 | Kaduchak et al. ............ 348/370 |

OTHER PUBLICATIONS

X. Cheng, Y. Liu, D. Irimia, U. Demirci, L. Yang, L. Zamir, W. R. Rodriguez, M. Toner and R. Bashir, Lab Chip, 2007. 2007(7): p. 746.

A. D. Elder, S. M. Matthews, J. Swartling, K. Yunus, J. H. Frank, C. M. Brennan, A. C. Fisher and C. F. Kaminski, Opt. Express, 2006. 14(12): p. 5456-5467.

D. R. Matthews, H. D. Summers, K. Njoh, R. J. Errington, P. J. Smith, P. Barber, S. Ameer-Beg and B. Vojnovic, Appl. Optics, 2006. 45(9): p. 2115-2123.

J. Emmelkamp, F. Wolbers, H. Andersson, R. S. DaCosta, B. C. Wilson, I. Vermes and A. van den Berg, Electrophoresis, 2004. 25(21-22): p. 3740-3745.

A. Daridon, M. Sequeira, G. Pennarun-Thomas, H. Dirac, J. P. Krog, P. Gravesen, J. Lichtenberg, D. Diamond, E. Verpoorte and N. F. de Rooij, Sens. Actuator B-Chem., 2001. 76(1-3): p. 235-243.

X. Heng, D. Erickson, L. R. Baugh, Z. Yaqoob, P. W. Sternberg, D. Psaltis and H. Yang, Lab Chip, 2006. 6(10): p. 1274-1276.

D. Lange, C. W. Storment, C; A. Conley and G. T. A. Kovacs, Sens. Actuator B-Chem., 2005. 107(2): p. 904-914.

C. L. Curl, C. J. Bellair, T. Harris, B. E. Allman, P. J. Harris, A. G. Stewart, A. Roberts, K. A. Nugent and L. M. D. Delbridge, Cytom. Part A, 2005. 65A(1): p. 88-92.

W. Z. Song, X. M. Zhang, A. Q. Liu, C. S. Lim, P. H. Yap and H. M. M. Hosseini, Appl. Phys. Lett., 2006. 89(20).

C. Zimmer, B. Zhang, A. Dufour, A. Thebaud, S. Berlemont, V. Meas-Yedid and J. C. Olivo Marin, IEEE Signal Process. Mag., 2006. 23(3): p. 54-62.

J. Garcia-Sucierquia W. Xu, S.K. Jericho and P. Klagges, M.H Jericho and H. Juergen Kreuzer Digital in-line holographic microscopy 2006, Applied Optics, vol. 45, 5, 636-850.

P.E. Norgren of Perkin Elmer, 1969 Annals of the New York Academy of Sciences. 157, 514-524.

Francis T. S. Yu, Introduction to Diffraction, Information Processing, and Holography, The MIT Press, Cambridge, MA, 1973, pp. 359-360, chapter B (appendix).

Joseph W. Goodman, Introduction to Fourier Optics, McGraw-Hill, San Francisco, 1968, pp. 34-37, chapter. 3.

Lange D et al: "A microfluidic shadow imaging system for the study of the nematode Caenorhabditis elegans in space" Sensors and Actuators B, Elsevier Sequoia S.A., Lausanne, CH, vol. 107, No. 2, Jun. 29, 2005, pp. 904-914, XP004899929 ISSN: 0925-4005.

Shapiro et al: "Biological imaging by soft x-ray diffraction microscopy" *PNAS* 2005;102;15343-15346; originally published online Oct. 11, 2005; doi: 10.1073/pnas.0503305102.

Chapman et al: "High Speed Lensless Integrated Proximity Sensor". http://www-als.lbl.gov/als/science/sci_archive/114biolensless.html.

http://www.cyto.purdue.edu/hmarchiv/2004/1577.htm.
http://www.nasatech.com/Briefs/Aug98/NPO20218.html.
http://www.nasatech.com/Briefs/Sept02/NPO20610.html.

Biochips Open Day presentation and poster (Apr. 5, 2006), PowerPoint Slideshow and Poster.

Set for Britain, Top young researchers in Bioscience, poster presentation at House of Commons (May 8, 2006), Poster.

J. Beuthan, O. Minet, J. Helfmann, M. Herrig and G, Muller, Phys. Med. Biol., 1996. 41(3): p. 369-382.

James P. Ryle, et al., "Digital in-line Holography of Biological Specimens", 2006, 8 pages, vol. 6311, Proc. of SPIE.

L. Repetto, et al., "Lensless Digital Holographic Microscope with Light-Emitting Diode Illumination", May 15, 2004, 3 pages, vol. 29, No. 10, Optics Letters, Genova, Italy.

* cited by examiner

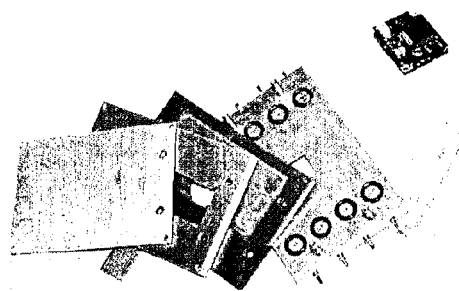
Figure 5
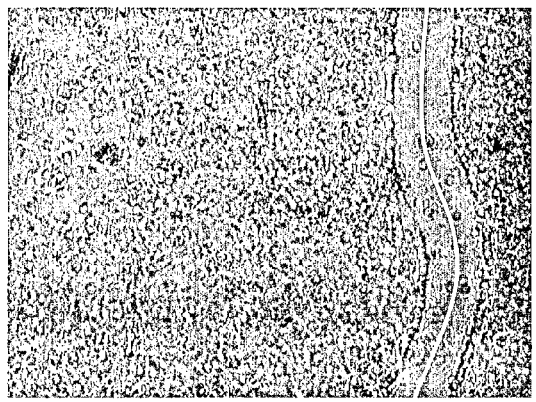
Figure 6
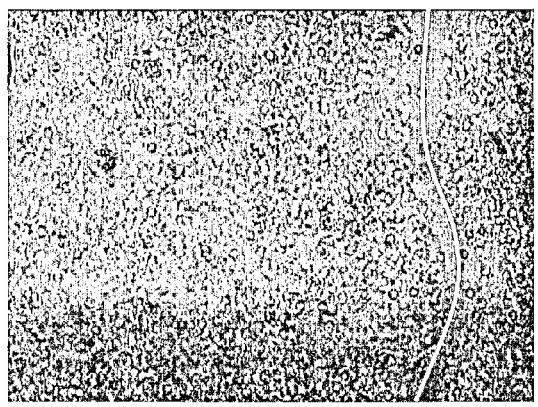 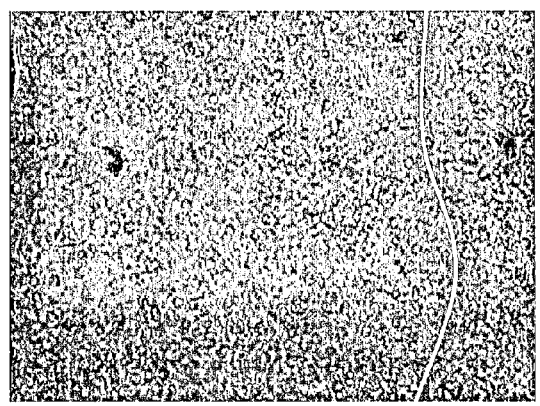

- Panel shows total number of detected cells per frame.
- Exponential fit to the data gives a doubling time of 28 hrs.

DETECTING OBJECTS

FIELD OF THE INVENTION

The present invention relates to apparatus and methods for detecting biological cells, other biological structures and/or other objects of interest. The apparatus and methods can be used, for instance, for mapping the positions of and/or tracking movements of the objects (e.g. cells). Embodiments of the invention are especially (although not necessarily exclusively) suited to mapping and/or tracking live cells, for example live mammalian cells. The apparatus and methods can be useful in automating a wide range of live cell-based assays and can be incorporated, for example, in lab-on-chip devices, microfluidic platforms or hand-held devices.

BACKGROUND

There have been significant advances in recent years in the development of microfluidic/lab-on-a-chip (LOC) cellular assays, with numerous papers detailing different detection/analysis methods which may be used in such devices [1-5]. However, these all tend to be interrogation methods which provide measurements of specific parameters, e.g. a change in intensity or lifetime of a fluorophore. A more general monitoring device would find wider application. At present all optical imaging of biological samples, with a few exceptions, is still undertaken on large expensive microscopes that obviously do not exploit many of the advantages offered by LOC devices, such as small size and low cost.

One notable exception is the optofluidic microscope (OFM) [6] developed by Heng et al., which has a resolution comparable to that offered by conventional microscopy (measured to be 490+/−40 nm). This method however, relies on the sample being moved across the sensor at a known velocity making the OFM unsuitable in situations where the cell/sample/object of interest remains fixed or moves at an unknown velocity, such as in clonogenic or chemotaxis type assays.

Lange et al. developed a shadow imager [7] for studying the effects of space flight on nematode *Caenorhabditis elegans*. In this system *C. elegans* are placed directly on top of an area imager and illuminated with collimated light, thereby casting a shadow onto the sensor. The resolution of the resultant image is inherently set by the pitch and pixel size of the video camera chip, making (in practice) the detection of single cells (e.g. mammalian cells with a diameter of $=15\,\mu m$) extremely difficult if not impossible. Also most cells are transparent at visible wavelengths and thus may not produce a discernable shadow.

Current technologies for monitoring live cells over time are largely reliant on manual intervention and expertise; automatic technologies are immature or bulky and expensive.

Any application where cells have to be kept alive and viable for extended periods of time (several days to weeks) requires the use of an incubator. Large, laboratory-based incubators are generally used, and these maintain a suitable temperature and gas mixture environment. Monitoring of the cells must be performed on a microscope, which requires an operator to transfer the dish or flask of cells from the incubator. A trained operator usually then views the cells using phase-contrast microscopy.

Automation of this process may be performed by the creation of an incubation chamber that surrounds the microscope, but keeping cells viable in this environment is usually more problematic. This approach also requires the use of an expensive automated microscope. Detection and tracking of the cells by processing the images from the phase-contrast microscope is also possible in principle, but is difficult in practice because of the large variability in the visual appearance of cells when visualized in this manner. One attempt to automate and miniaturize this type of system is the CellIQ product (Chip-Man Technologies Ltd, Finland).

The use of point-source illumination with a coherent source (e.g. laser) has been described previously [13, 14, 15], but with the intention to record holographic information. In such approaches, some form of reconstruction technique must be employed; recent approaches have relied on numerical or computational methods to perform the reconstruction. Furthermore, such approaches require the source diameter to be comparable or smaller than the wavelength of light used.

In some cases, Fraunhofer diffraction has been used to establish the power going into certain spatial frequencies by measurement of the relative brightness of an annular region [16]. In this instance, a laser source is used and only one or few objects are imaged.

SUMMARY OF INVENTION

Embodiments of the present invention are generally concerned with apparatus and methods in which the interactions between light from a light source (e.g. an incoherent light source) and a sample comprising a plurality of objects of interest (e.g. biological cells) are used to determine the location or number of the objects (e.g. cells) within the sample. Changes in the interactions can be used to track movements of the objects (e.g. cells) and/or other changes in the objects (e.g. cell division).

The sample is held between the source and a detector (i.e. in the transmission path of light from the light source to the detector) so that light from the light source is incident on an active light detecting surface of the detector subsequent to its interaction with the objects (e.g. cells) in the sample. The signal at the detector can be processed to recognise individual cells (or other objects of interest) within the sample based on characteristic patterns (e.g. diffraction patterns) created by the interaction between the light and the cell (or other object) and then to map the locations of the cells (or other objects) within the sample based on the detected patterns. Changes in relation to each cell (or other object), e.g. a change in position, will be reflected in changes in the patterns detected by the detector.

By adopting this approach, the movements (or other changes) in a great number of cells (or other objects) in a sample can be observed (at a macroscopic level) at one time.

Thus, embodiments of the invention can provide a cost effective, imaging modality suitable for observing live cell based assays. The system may use a small aperture light-emitting diode (LED) and a charged-coupled device (CCD) array in an arrangement comparable to that used by Lange et al. However the geometries are arranged in such a way that the diffraction patterns due to cells are directly recorded (as opposed to the shadow images recorded by Lange et al), offering a cell 'signature' amenable to automated detection. By varying the CCD-cell distance, the size of the diffraction pattern on the CCD can be controlled.

BRIEF DESCRIPTION OF DRAWINGS

An embodiment of the present invention will now be described by way of example only with reference to the accompanying drawings, in which:—

FIG. 5 shows another practical example of an apparatus according to an embodiment of the present invention (CyMap), integrated within a microfluidic platform;

FIG. 6 shows images of a 'wound healing' assay involving cell migration captured with the CyMap apparatus;

DESCRIPTION OF EMBODIMENTS

Figures 1A, 1B:
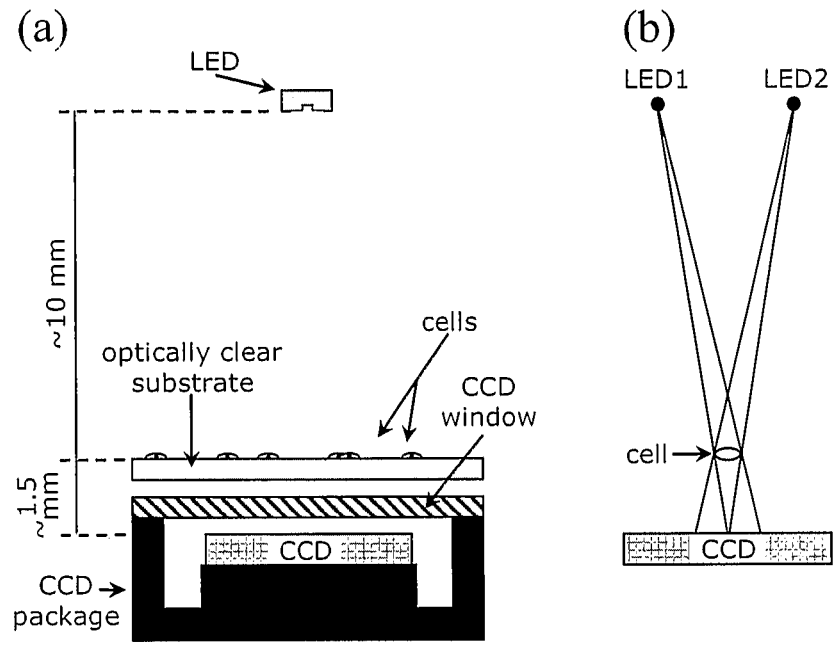
FIG. 1a shows a schematic representation of the imaging setup according to an embodiment of the present invention used to observe live cells.
FIG. 1b shows a schematic illustration of the use of multiple light sources to determine a three dimensional location of a cell's position.

In the description below, apparatus according to embodiments of the invention is generally referred to as the 'CyMap' device. In some of the Figs., the CyMap device is labelled "Biochip" or "Biochip head".

Overview of Embodiments

The CyMap device is a novel miniature device to optically image mammalian cells or other transparent or opaque particles, to map their locations and to track their movements. The principal features of the device are that:

No image-forming optical components are utilized.
No optical focusing methods are required.
No cell staining or other markers need to be used to 'image' live or viable cells.
The device locates cells by deriving a 'cell signature signal', i.e. it is the interaction of light with the cell, rather than an image of the cell which is recorded.
The fate of cells (e.g. movement, division etc.) is thus readily and uniquely identified.

Only standard cell culture techniques need to be employed for cell preparation.

Cells can be imaged in standard culture plates, dishes and flasks.

Three-dimensional cell location information can be obtained.

Very low light intensities can be used in the imaging process, which can be at non-toxic wavelengths (~600 nm).

Only an electronic display of the imaged field is obtained, i.e. no optical image visible by eye is available.

No internal features of the cells can be distinguished, but could be derived indirectly through signal processing methods.

The field of view is fixed at time of construction by the CCD's active area and can only be reduced using electronic means (electronic zoom).

The advantages of the device are that:

The device is easily miniaturized (down to 30×30×30 mm or less) and can thus be readily placed inside an incubator or similar temperature- and gas-controlled environment, or within a hand-held device.

The image acquisition process is fast and the imaging process is not photon-limited, even with low levels of illumination.

The device is focus free—i.e. afocal.

The device is light-efficient because there are no optical elements in the light transmission path.

No critical mechanical components are utilized in the construction.

The component cost of the device is very low.

No moving parts are utilized other than possible means of introducing the 'sample' into the device.

The implementation of the device is readily modified to allow for image acquisition of multiple fields, e.g. collection of data from multi-well plates by movement of the device relative to the multi-well plates and/or the use of multiple image capture devices.

The range of assays which can be performed is defined by software algorithms used.

The potential applications of the device are listed below and not necessarily limited to the items listed:

Any quality-control application where cell growth needs to be monitored with the advantage over current 'sampling' methods that remote monitoring is feasible, e.g. cell production.

Any application involving clonogenic cell assays.

Any application where cell division or mitosis needs to be monitored.

Any application where cell lineage needs to be monitored or tracked, e.g. stem cell research.

Any application where cell movement resulting from the influence of chemical or biological agents is monitored e.g. chemotaxis or similar cell migration assays.

Applications involving 'wound-healing' assays taking place in cell cultures.

Any application where the adherence of cells needs to be monitored.

Any application requiring knowledge of cell location coordinates where the speedy determination of these coordinates, particularly over large fields of view, and their transfer to a more sophisticated imaging system, along with the sample, is required.

A very wide range of techniques currently reliant on a complex microscope to monitor changes in cell position and viability over time, at low magnification where phase contrast methods are most probably utilized.

Any application requiring portability or miniaturization or disposability (e.g. specialised home assay kits).

Any application which is associated with 'Lab-on-Chip' technologies, where the unit is integrated as part of a larger cell analysis system.

Any application for monitoring non-cellular particles or non-mammalian cells in a similar fashion.

In general, applications where live cells are used are preferred. However, the device also may have applications where fixed cell preparations are used.

In common with some of the prior art referred to above, embodiments of the present invention record a diffraction/interference pattern. However, with the approach adopted by the present invention, and in contrast to the prior art, an incoherent light source may be utilized, and its diameter is relatively uncritical. Although minimal structural information from the object is available, no reconstruction steps are required and the object is inferred from its diffraction pattern.

Advantageously, in particular as a non-coherent light source is utilized, the imaged field in embodiments of the present invention can be made as large as required (limited only by the availability of large-area sensors).

Overview of the Device

The device geometry for one exemplary embodiment of the invention is arranged as outlined in FIG. 1a. The stated LED-cell and CCD-cell distances are examples of typical settings used and may be varied depending on the circumstances and requirements.

Resonant Cavity LEDs [8], emitting at 650 nm, with 60 µm diameter apertures proved suitable light sources. The exact aperture size was found not to be critical with diameters in the range 1 to 80 µm being successfully tested (Other successfully implemented light sources include a broad area LED with a 6 µm pin hole (Comar, 06HP16) or a multimode optical fibre). While sources at other visible light wavelengths, or combinations of wavelengths, can be used, redder sources are less toxic to live cells. It is also possible to obtain images with larger area light sources but image quality is affected as the interference patterns can become blurred, making object recognition more difficult.

In this example a Sony EXview (ICX279AL, ¼" format, 2.4×3.2 mm active area) monochrome CCD was used as the detector.

By adopting the arrangement outlined in FIG. 1a it is possible to record directly the diffraction/interference patterns generated by the cells of interest (but equally other micron sized objects). As each cell produces its own individual interference pattern this technique may be used to produce a real time map of multiple cell positions. As the cells have a refractive index slightly greater than that of water (1.33) and their surrounding growth media [9-11] they will also act as crude lenses, phase shifting and focusing the transmitted light. Hence more complex interference patterns may be formed than those predicted using aperture diffraction theory. A simple interference model, based on a cells/objects lensing properties, has been developed which reasonably reproduces experimentally recorded line profiles of 10 µm beads, imaged using CyMap.

In an enhancement to the basic arrangement seen in FIG. 1a, by using multiple point light sources, individually energised and sequentially imaged, a cell's position in three dimensional space may be determined. To explain, as illustrated in FIG. 1b the position of the cell obtained when illuminated by LED1 will appear shifted as compared to its position when illuminated by LED2. This shift in cell position can then be used to calculate the height of the cell above the CCD. Alternatively, given prior knowledge of an object, it is also possible to infer its height from the diameter of its diffraction pattern using a single source. The larger the diffraction pattern, the higher the position of the object above the CCD.

Figure 10:
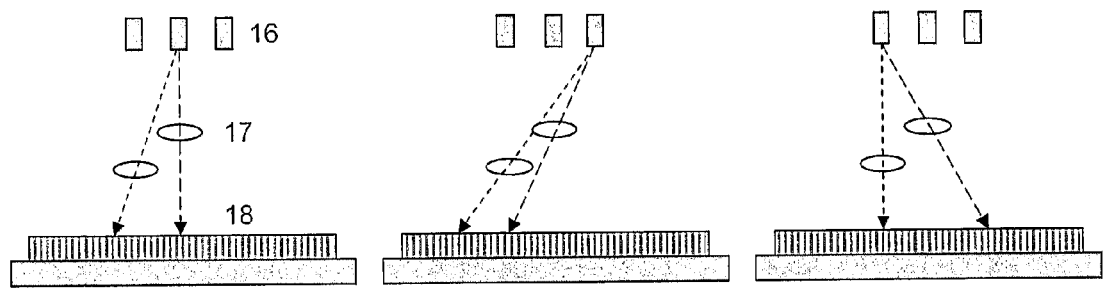
FIG. 10 schematically illustrates the use of multiple point light sources (minimum of two, but more appropriately three) to allow three-dimensional localization of objects to be determined.

FIG. 10 shows a similar multiple light source arrangement, in this case with three light sources (16) used to determine the position of objects (17). The sequence of images in FIG. 10 shows how the optical signatures from objects at different heights appear in different positions on the detector focal plane (18) as the light sources are sequentially energised.

Figure 1C:
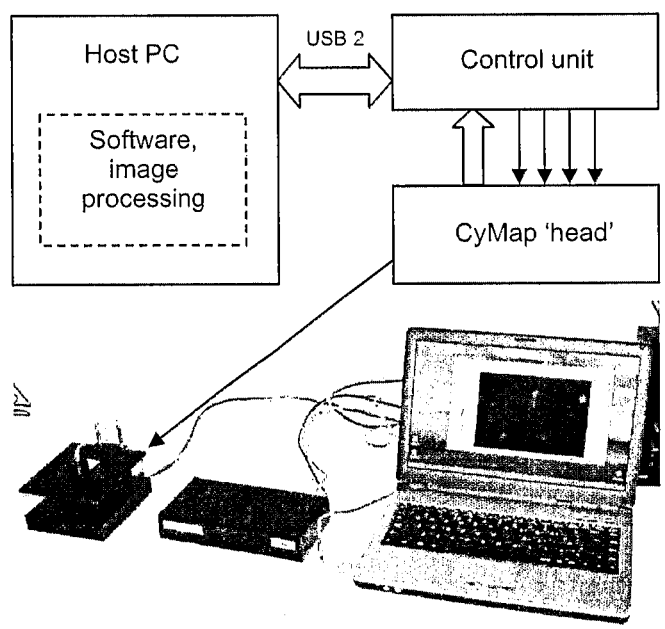
FIG. 1c shows one exemplary practical apparatus (referred to as CyMap) in accordance with an embodiment of the present invention.

FIG. 1*c* shows one exemplary practical system (referred to as CyMap) implementing the concepts discussed above. The system includes an imaging head unit (configured in accordance with the arrangement seen in FIG. 1*a*), a power supply and control unit and a standard, laptop, host PC that can be used to capture and display data from the imaging head unit.

Principles of Operation

The CyMap device consists of three principal elements: a near point-like light source, an image collection device and a recording and display device. These elements can be implemented in numerous ways, examples of which are listed below. In addition, the images obtained can be quantified in a number of ways, although in practice, methods relying on software running a variety of image processing algorithms are most convenient.

(1) Light source: emission area should be as small as possible consistent with delivering a flux which is intense enough to drive to full-scale the imaging detector. The light source is preferably a point light source, and this term is intended to include a point-like light source and/or a near point-like light source. In practice a red light emitting diode, suitably apertured to a diameter of around 100 microns or less has been found to be adequate.

(2) Image collection device: an electronic area detector, also referred to as an active light detecting surface implemented in CCD or CMOS technology, or any other pixelated technologies, or other technologies appropriate to the electronic recording of an image, is most suitable. However, for certain specialized applications, indirect image recording, using light-sensitive film may be more appropriate.

(3) Image recording and display device: this is intimately related to the image collection device and clearly must be compatible with it. In the case of electronic imagers, it should be able to handle either analogue or digital signals, depending on the output format of the imager. In its simplest form, a CCTV analogue monitor is adequate, though a more practical solution would utilize a means of capturing the image in digital format for display on a computer screen. In practice, pixel dimensions of around 10×10 microns or less are required and modern CCD devices in ¼" or greater formats, are acceptable. Consequences of improved resolution are superior object signature recognition, although this may be at the expense of increased processing speed. Processing speed is also affected by total pixel number, i.e. by the imager area.

The software algorithms are wide-ranging, and can be developed in any language and be executed on any platform (so long as they are compatible with the device) but fall into the following categories:

(1) Software tools that capture the image, and/or a sequence of images, and control the image collection device and light source.

(2) Software tools that 'recognise' the cell/object signature. The skilled person will be aware of many examples of suitable software tools including e.g. those that 'recognise' the cell/object signature through the application of a matched filter or similar kernel across the image and provide an output proportional to the correlation of image features with the kernel: a good 'match' provides enhanced output. Other examples include approaches based on: 'thresholding'; Hough transforms; 'watershed'; and frequency (e.g. Fourier) or wavelet transforms.

(3) Software tools which act on the 'found' objects and track their positions. Examples include model-based/rule-driven tools and Bayesian/probabilistic methods.

(4) Software tools which act on the raw image or on a sequence of images, and provide a signal where there are dynamic changes in the image, e.g. the spatial frequency content of the image is changing or the wavelet components of the images are changing, thus enhancing specific events such as cell attachment and mitosis, where the object optical signature is changing. Such tools are geared towards event detection.

In some cases, where modern CCD imagers are used for example, some of the software functions described above may be embedded in/be integral with the imager itself.

Figure 7:
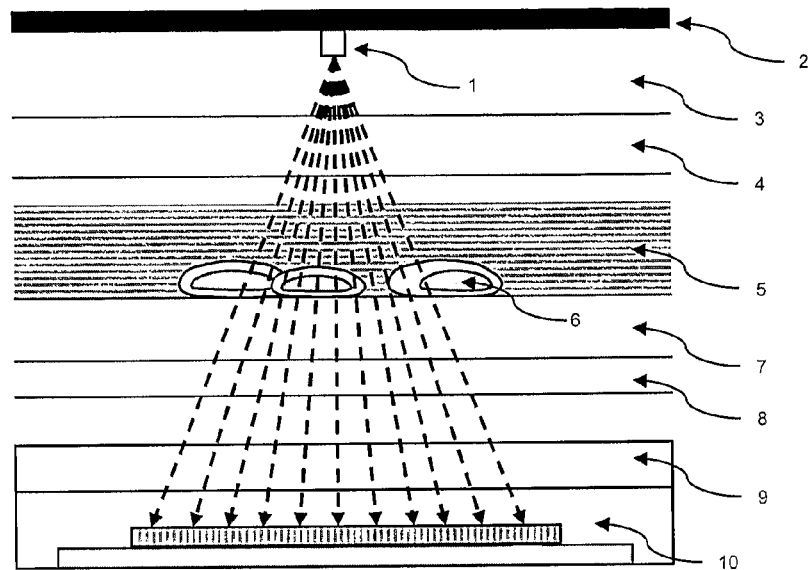
FIG. 7 schematically shows the principle elements of an example of the CyMap apparatus.

A simplified diagram of the device, used to help illustrate its operation, is shown in FIG. 7, from which the principle elements of the CyMap device can be seen. A point-like incoherent light source (1), on support (2) emits a cone of light which travels through a possible air gap (3), possibly through a transparent substrate (4) and through the 'sample' (6), likely to be immersed in a fluid (5) towards an area imager (10). The sample contains objects of interest e.g. cells (6) immersed a liquid medium (5) contained between two optically clear substrates (4, 7). In some cases, the upper substrate (4) and an internal air gap are not present (e.g. an open cell dish), while in other cases, additional optically transparent substrates (8, 9) may also be eliminated. In general, however, the sample chamber may be held on a further optically clear substrate (8) separated by a small air gap from the imager protective window (9).

The sample to be imaged, usually contained in a flask or other sample-holder (e.g. open cell dish or multi-well plate), is placed at a sample holding location in close proximity to the input window of the imager. Placement in direct contact with the window is also acceptable but perhaps not advised, due to potential problems with damage to the window through long-term use. Several optically clear substrates are acceptable, ideally the distance between the imager and the cell support interface is kept as short as possible as this reduces the chances of interference patterns from adjacent cells overlapping.

Figure 9:
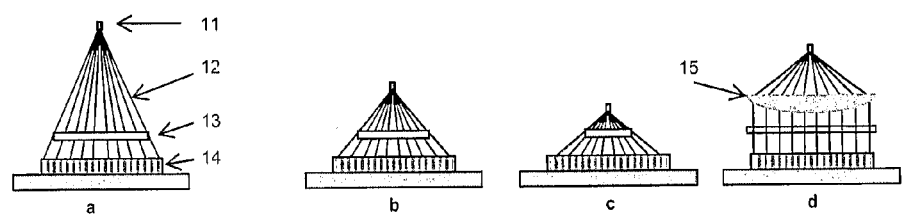
FIG. 9 illustrates possible change in CyMap sample field of view with variation of source-to-sample distance.

The closer this distance is, the higher the quality of the recorded data. However, as the distance is reduced, the diameters of the light patterns, which define the cell signature, are also reduced and this places increased constraints on the resolution of the imager, which must recognize this signature. FIG. 9 schematically illustrates this possible change in CyMap sample field of view with variation of source-to-sample distance. The point-like source (11) emits rays (12), through the sample (13) onto the area imager (14). As the distance between the source and the sample is reduced, from (a) to (b) to (c), the field of view associated with sample (13) is reduced.

An alternative approach illustrated in FIG. 9(*d*) is to use a lens (15) to collimate the output from the point source. With appropriate selection of the lens, this allows the field of view to substantially equal that afforded by the sensor dimensions.

The light patterns may comprise (or be) diffraction patterns. Diffraction patterns are broadly classed as Fresnel or Fraunhofer diffractions; this distinction is based on the various approximations that can be made in models of optical field propagation associated with phase conditions using e.g.

Figure 8:
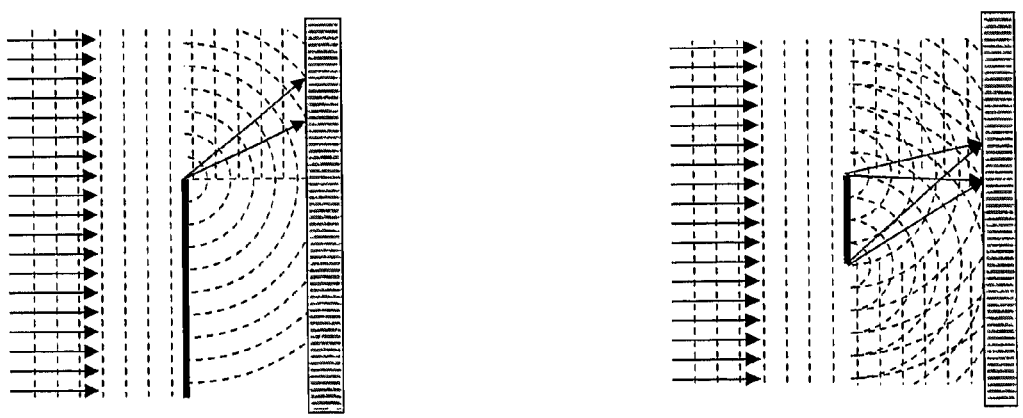
FIG. 8 is a schematic illustration of diffraction from an edge (left) and from a small, finite-sized absorbing object (right)

Huygens' Principle or Green's Function [17, 18] and whether a near-field or far-field observation is used. In both cases regions that, in geometrical optics, would contain transitions between light and dark, give rise to oscillatory signals via diffraction and interference effects. FIG. 8 is a schematic illustration of diffraction from an edge (left) and from a small, finite-sized object (right) and illustrates basic diffraction principles.

In our case, the Fresnel approximation should be applicable. However, the object of interest (the cell) itself behaves as a crude lens and thus more complex patterns are likely to result, particularly from phase changes associated with changes in refractive index between sub-cellular structures (e.g. nucleus vs. cytoplasm; typically 1.39 vs. 1.35).

At object-detector distances greater than $d^2/\lambda$, where d is the diameter of the diffracting object and $\lambda$ the wavelength of the light, it is the Fraunhoffer approximation which is applicable, while the near-field, or Fresnel derivation, is applicable at shorter distances. Assuming $\lambda$=600 nm and an object diameter of 20 μm, the transition distance is just over 660 μm, for 10 μm objects it is around 160 μm.

It is our understanding that we are more likely to be operating in the far-field, Fraunhofer mode. Here, the diameter of the first ring in the pattern is inversely proportional to the diameter of the diffracting object. This type of approach has been used in the past, where the detector records a hologram, formed by interference between the undiffracted illumination and the diffraction pattern of the object. In that instance subsequent reconstruction of detailed cell morphology including dry mass concentration would be possible, but would require different and more expensive apparatus (i.e. a coherent source and very high detector resolution e.g. using ultra-fine grain film).

Simple Interference Model

In many cases, the interaction of the light with a cell (or other object) can be understood by considering a simple interference model (not taking into account of diffraction), in which two waves interfere: one from the source itself; the second that has passed through the cell and been focussed.

Figure 18:
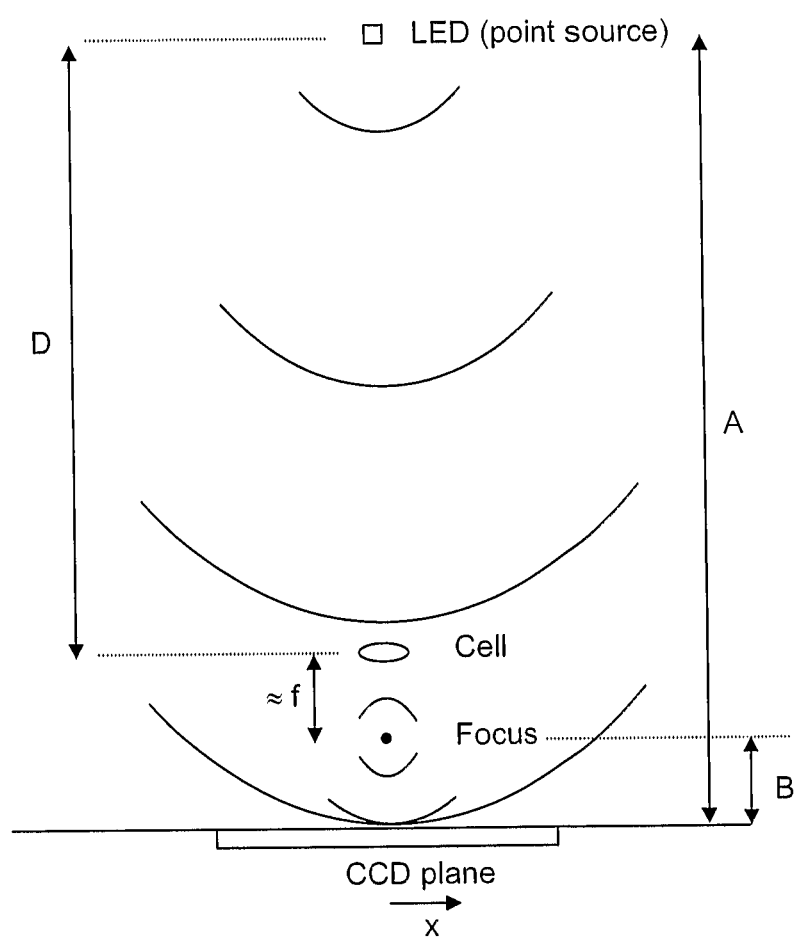
FIG. 18 is a schematic diagram illustrating parameters used in simple interference model.

With reference to FIG. 18, the light from the cell comes to a focus at some point near f (a focal distance) from the cell and at a distance B from the CCD.

The light field from the source can be written as:

$$E(x) = E_1(x)\exp\left(\frac{2\pi i}{\lambda}\sqrt{A^2 + x^2}\right)$$

and from the cell as:

$$E(x) = E_2(x)\exp\left(\frac{2\pi i}{\lambda}\sqrt{B^2 + x^2}\right)$$

where (by simple lens equation):

$$B = A - D - \frac{D}{\left(\frac{D}{f} - 1\right)}$$

Assumption—Although $E_1$ will probably be constant in x($E_1$(x)=$E_1$), $E_2$ will be a function of x and will probably be fairly Gaussian:

$$E_2(x) = E_2\exp\left(-\frac{x^2}{\sigma^2}\right)$$

where sigma will have some relation to D and f and the width of the cell (the NA of the cell lens).

The intensity at the CCD (I(x)) will then be the square of the complex sum of these two fields.

Let:

$$\theta_1(x) = \frac{2\pi}{\lambda}\sqrt{A^2 + x^2}$$

$$\theta_2(x) = \frac{2\pi}{\lambda}\sqrt{B^2 + x^2}$$

Then:

$$I(x)=(E_1 \cos \theta_1(x)+E_2(x)\cos \theta_2(x))^2+(E_1 \sin \theta_1(x)+E_2(x)\sin \theta_2(x))^2$$

Validating Simple Interference Model with 10 μm Beads

Figure 19:
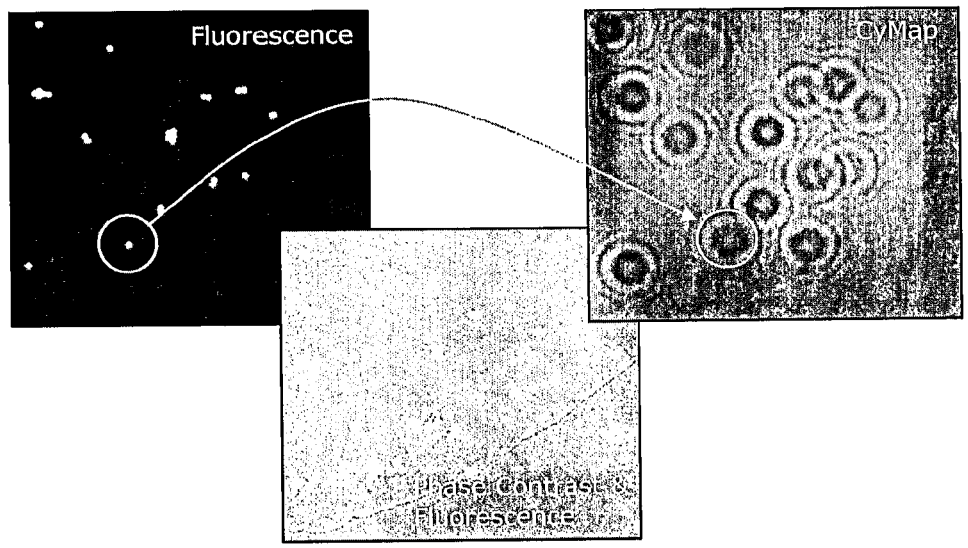
FIG. 19 shows images of 10 μm beads a) fluorescence, b) combined fluorescence and phase contrast, both images taken using a ×10 objective. c) section of a CyMap image showing the same field of view as in 19a & 19b.

10 μm beads were deposited onto a microscope slide and imaged using conventional phase contrast and fluorescence microscopy and the images compared to those obtained via CyMap, FIG. 19.

Figure 20:
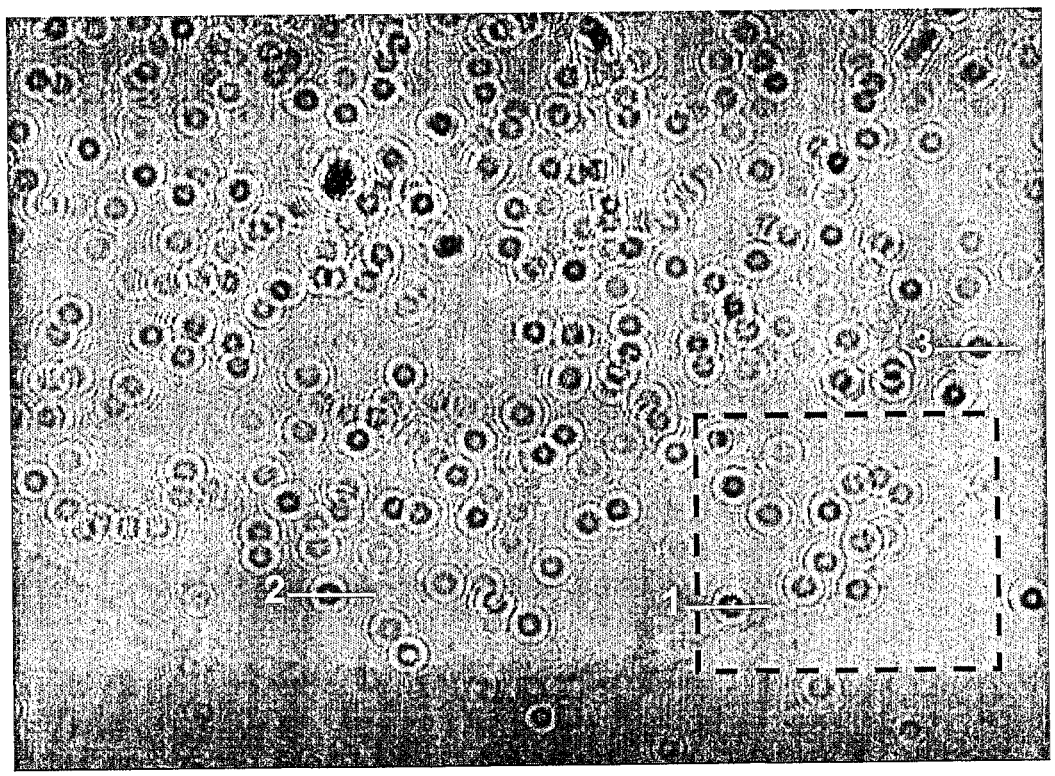
FIG. 20 shows the CyMap full field of view of 10 μm beads. Dashed box shows area of image presented in FIG. 19c. Numbered lines indicate the locations of line profiles displayed in FIG. 21.
Figure 21:
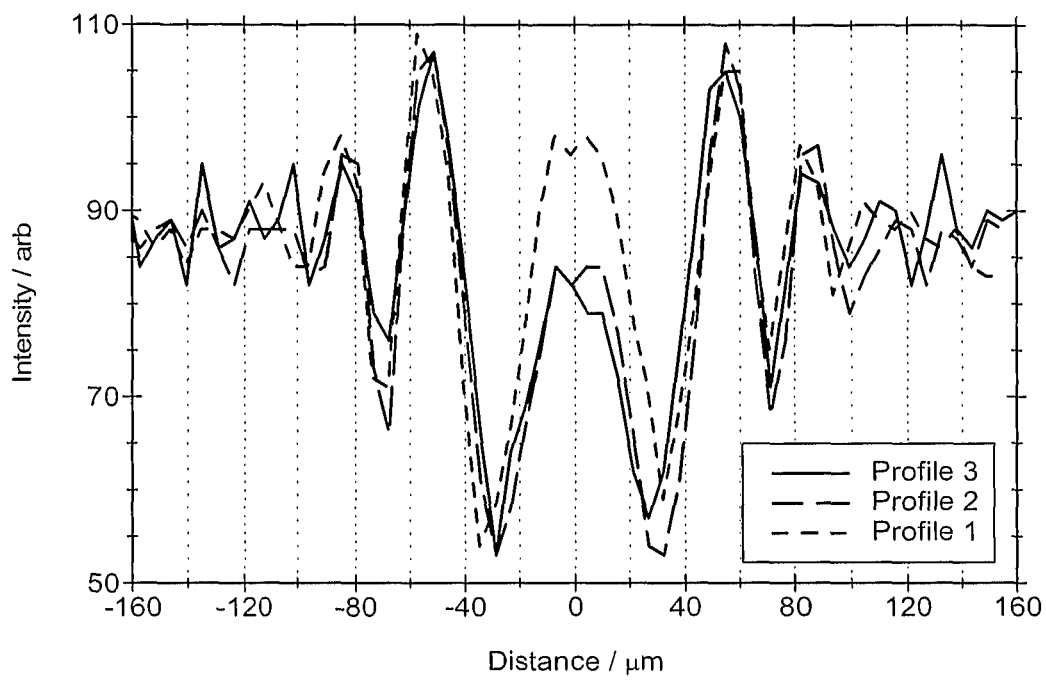
FIG. 21 shows line profiles of 10 μm beads taken from FIG. 20.

Line profiles were taken through the interference patterns (FIGS. 20 & 21) and the simple interference model was then used to fit the experimental data. The table below gives the parameters used in the fit. The parameters D, B and $\lambda$ were measured experimentally; the bead diameter and refractive index were taken from the bead data sheet and were used to calculate the focal length of the bead; the CCD pixel size was taken from the CCD data sheet; the values of $E_1$, $E_2$ and sigma were chosen arbitrarily to fit the amplitude and attenuation of the measured profiles.

| D | 9.5 mm | refractive index | 1.59 |
| B | 2.3 mm | pixel size | 5 μm |
| focus | 6.74 μm | $E_1$ | 0.5 |
| $\lambda$ | 652.86 nm | $E_2$ | 0.24 |
| bead diameter | 10 μm | sigma | 80 |

The images of beads showing the direct comparison with conventional microscopy indicate that the device cannot resolve two closely spaced beads. The size of the pattern recorded is in the region of 150 μm in our prototypes, arising from a cell that is of order 30 μm. Experimentation shows that the device can resolve two daughter cells from a single mitotic event. The mechanism for this is undetermined but it is thought that the cell nucleus contributes significantly to the signature and the separation of the daughter nuclei is sufficient for them to be resolved shortly after mitosis.

Figure 22:
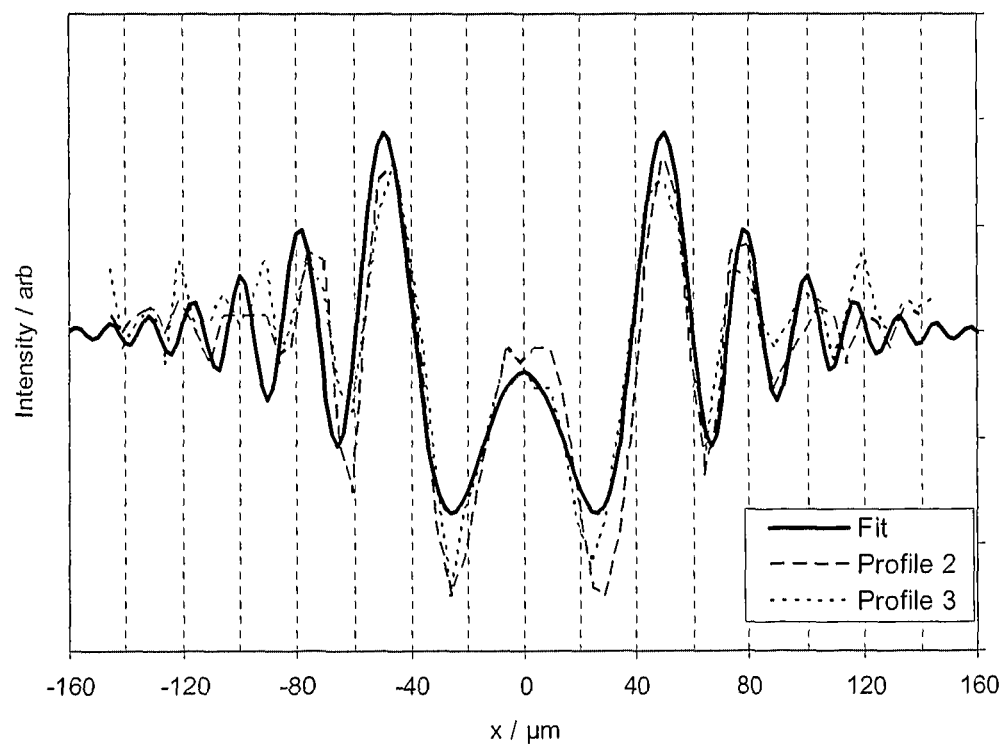
FIG. 22 shows in dashed & dotted lines the line profiles of the interference patterns produced by 10 μm beads and in solid line the fit to experimental data using a simple interference model.

As we can see from FIG. 22, using the simple interference model and the measured parameters a good fit to the experimentally recorded line profiles is achieved. When fitting the data only the value D was varied around the measured value. However it should be noted that being an interference model it is sensitive to small changes in any of the experimentally measured value, such as the values B and $\lambda$. To achieve an exact and robust fit to the experimental line profiles a rigorous model incorporating the full diffraction theory would need to be employed.

EXAMPLE IMAGES AND IMPLEMENTATIONS OF THE CYMAP DEVICE

Example 1

Figure 2:
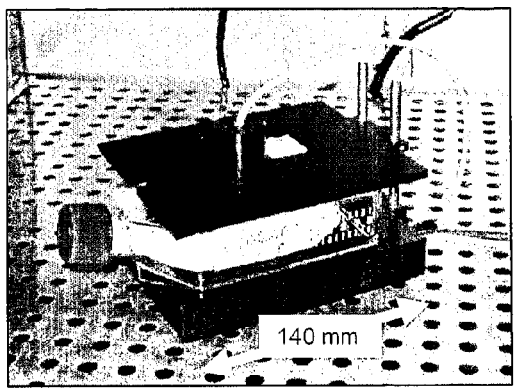
FIG. 2 show an example of a CyMap apparatus and typical raw images from the apparatus.
Figure 2:
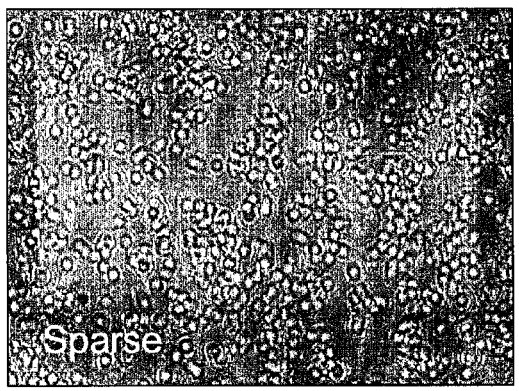
Figure 2:
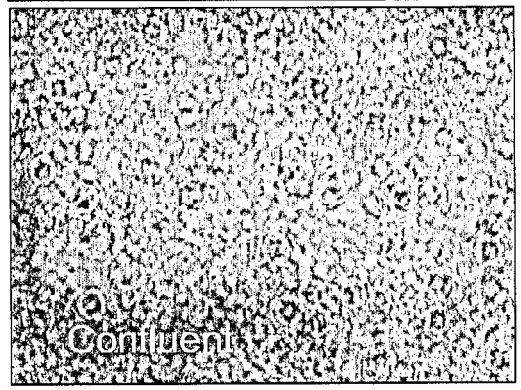
Figure 2:
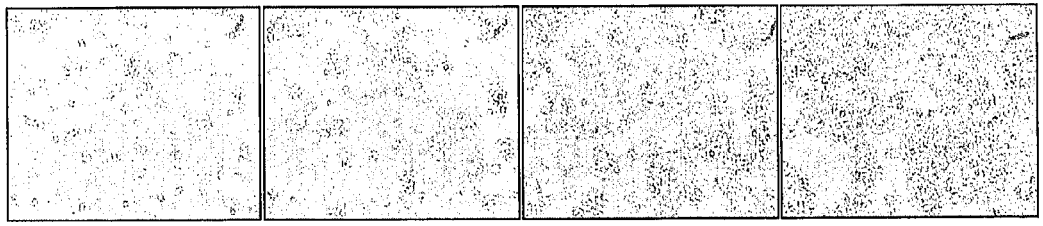

FIG. 2 shows an example of a CyMap apparatus used inside an incubator (top right image) and typical raw images of cells plated in a T75 flask (middle two images) showing a sparse and near-confluent cell culture. Standard cell preparation and cell growing techniques were used. The flask was imaged throughout the cell growth process, i.e. the flask was located within the CyMap and within the incubator throughout. Selected images at successive time points over a 4 day period, from a 'movie' sequence, are shown in the lower four panels.

Example 2

Figure 3:
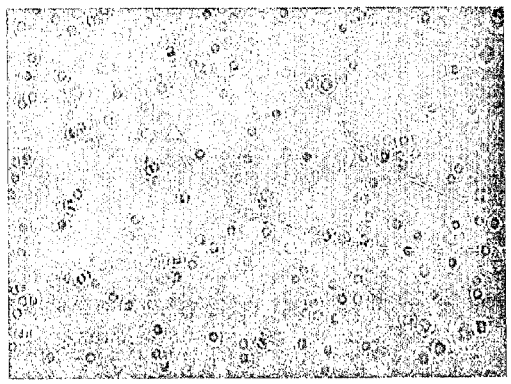
FIG. 3 shows 'Raw' CyMap image (left) and image-processed result (right)
Figure 3:
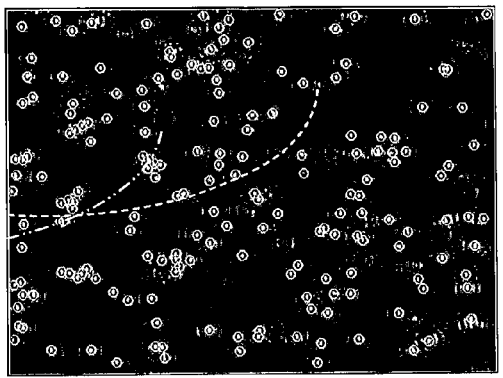

FIG. 3 shows 'Raw' CyMap image (left) and image-processed result (right). In this instance all attached cells have been 'found', one example cell is outlined with a white ring and its location mapped on the raw image (short-dashed line). Note that a 'floating' or unattached cell (long-dashed-dot line) is not identified and is rejected by the image-processing software;

Example 3

Figure 4:
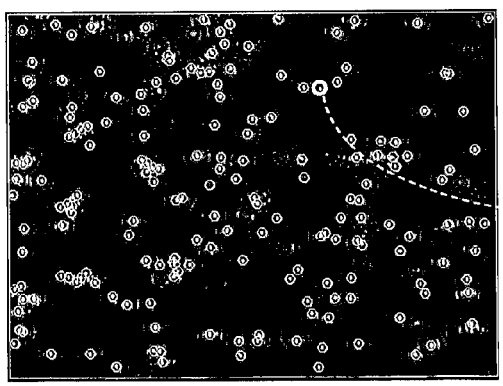
FIG. 4 shows an example of cell coordinate tracking.
Figure 4:
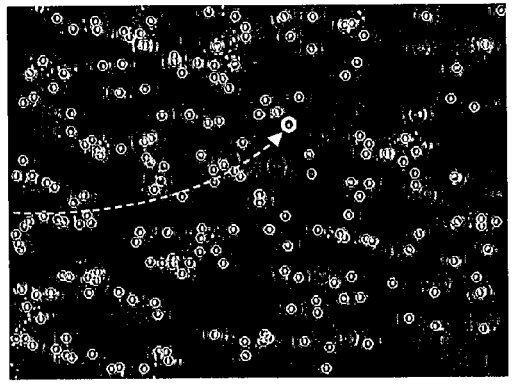

FIG. 4 shows an example of cell coordinate tracking, showing results of image-processing data taken over approximately 24 hours, with a time-interval of 4 hours between the left and right images. The 'movement' of one individual is identified by the dashed line and associated white circles;

Example 4

FIG. 5 shows another practical example of an apparatus according to an embodiment of the present invention (CyMap), where it is integrated within a microfluidic platform, with four inlet and four outlet channels, using a single area sensor (upper right of the image). The component 'layers' of the assembly would normally be clamped together; overall dimensions are ~100 mm×60 mm;

Example 5

FIG. 6 shows images captured with a CyMap apparatus showing a 'wound healing' assay. Following growth to confluency of U2OS cells, a channel was scored through the cells using a plastic scrapper (upper image). The preparation was then recorded every 2 mins for 14 hours. The white line overlay indicates the path of the 'wound'. The lower images are taken some 6 hours (left) and 12 hours (right) into the 'wound healing' process.

Example 6

Figure 11:
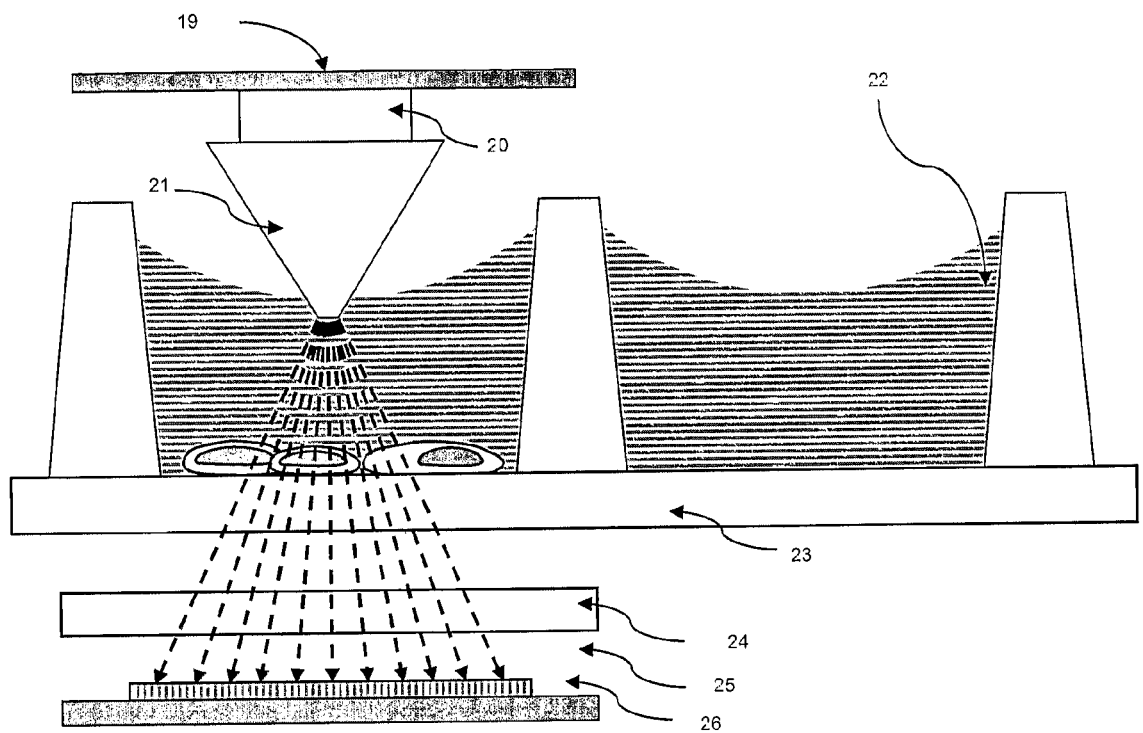
FIG. 11 shows, schematically, another alternative practical implementation of an apparatus in accordance with an embodiment of the invention (CyMap), when used with e.g. multi-well plates.

FIG. 11 shows an alternative implementation of the CyMap device that can be used with multi-well plates or other similar cell culture containers which are not fully enclosed and or where the presence of a meniscus would alter the optical paths between the source and sample; tight control of liquid level and viscosity would then be required.

In this implementation, a large light source (20) is held on a support (19) and is optically coupled to a truncated axicon or tapered optical fibre (21). The sample is held within a multi-well plate or similar substrate (23), immersed in fluid (22). The effective light source is thus point-like and the image information is transported by light rays travelling through an optically transparent imager window (24), through a short air gap (25) onto the area imager (26). More than one such source can be used to provide three-dimensional information as described above and separate imagers and light sources can be used to acquire information in parallel from adjacent areas or wells. An array of such light guides (truncated axicon or tapered optical fibre) could be built into the lid of the multi-well plate. A single light source could serve all wells simultaneously.

Example 7

Figure 14:
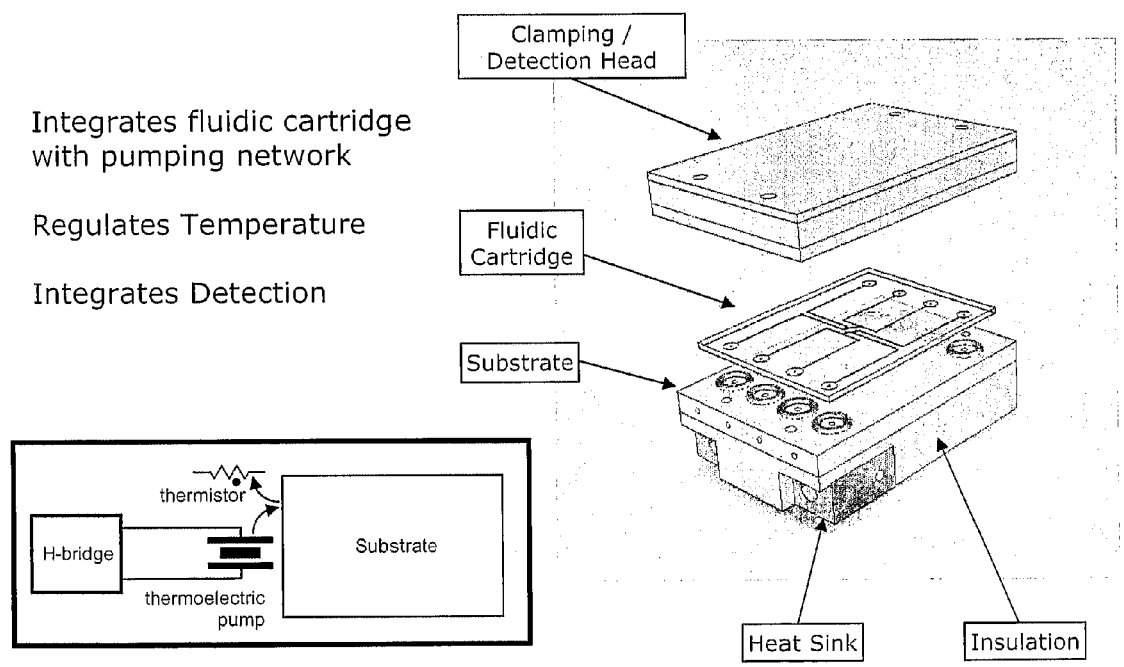
FIG. 14 schematically shows an apparatus in accordance with an embodiment of the present invention in which the CyMap device ("Biochip head") comprises a micro-fluidic platform.

FIG. 14 schematically shows an apparatus in accordance with another embodiment of the present invention in which the CyMap device ("Biochip head") comprises a micro-fluidic platform.

Figure 12:
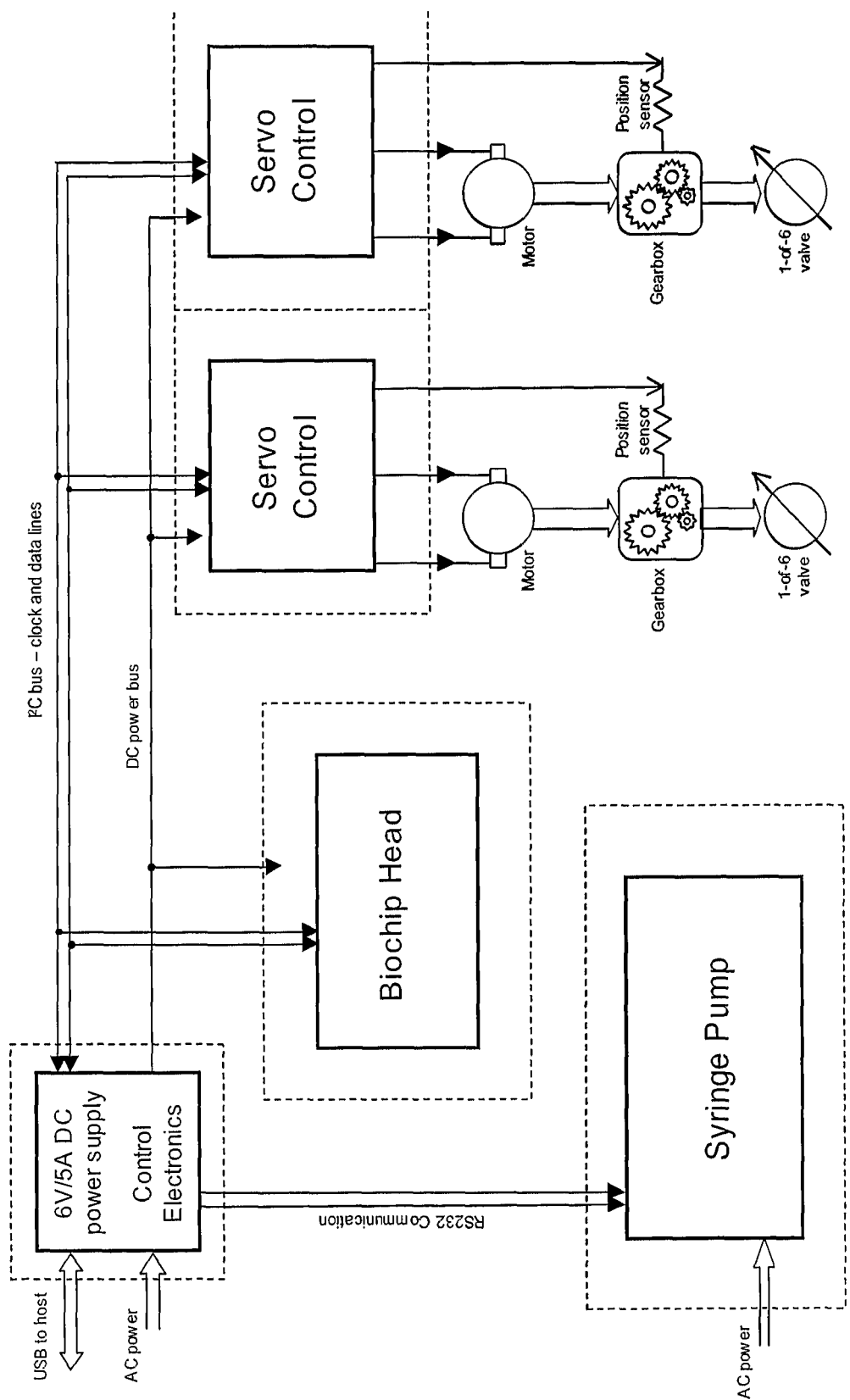
FIG. 12 schematically shows components of a control system for an apparatus (see FIG. 14) in accordance with an embodiment of the present invention in which the CyMap device ("Biochip head") comprises a micro-fluidic platform, movement of fluid to and from the platform being controlled using pairs of valves (inlet and outlet) and a syringe pump.
Figure 13:
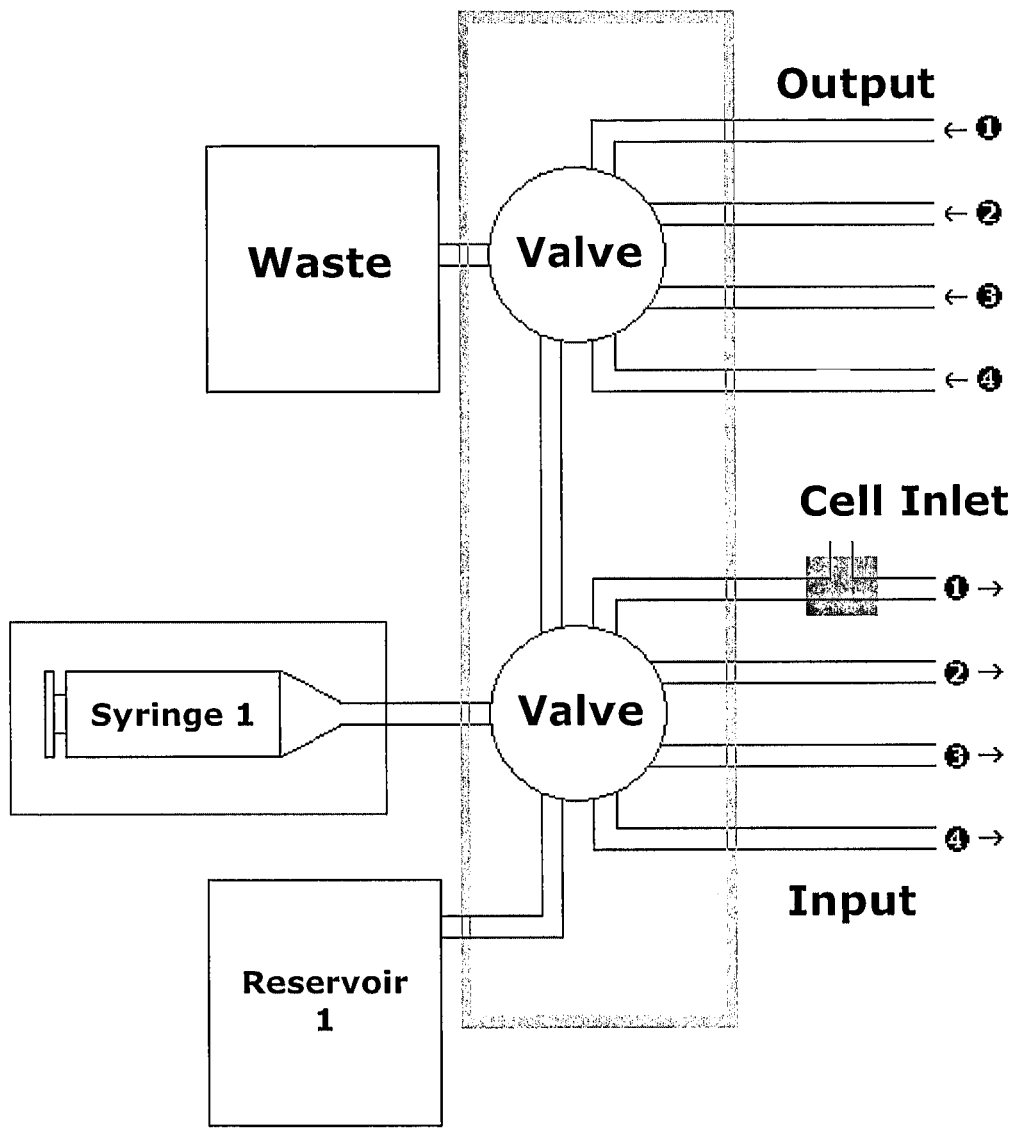
FIG. 13 schematically shows the fluidic connections between the valves and the syringe pump of the apparatus of FIG. 14.

FIG. 12 schematically shows components of a control system for the apparatus of FIG. 14. Movement of fluid to and from the platform is controlled using pairs of valves (inlet and outlet) and a syringe pump. The fluidic connections between the valves and the syringe pump are shown in FIG. 13.

Figure 15:
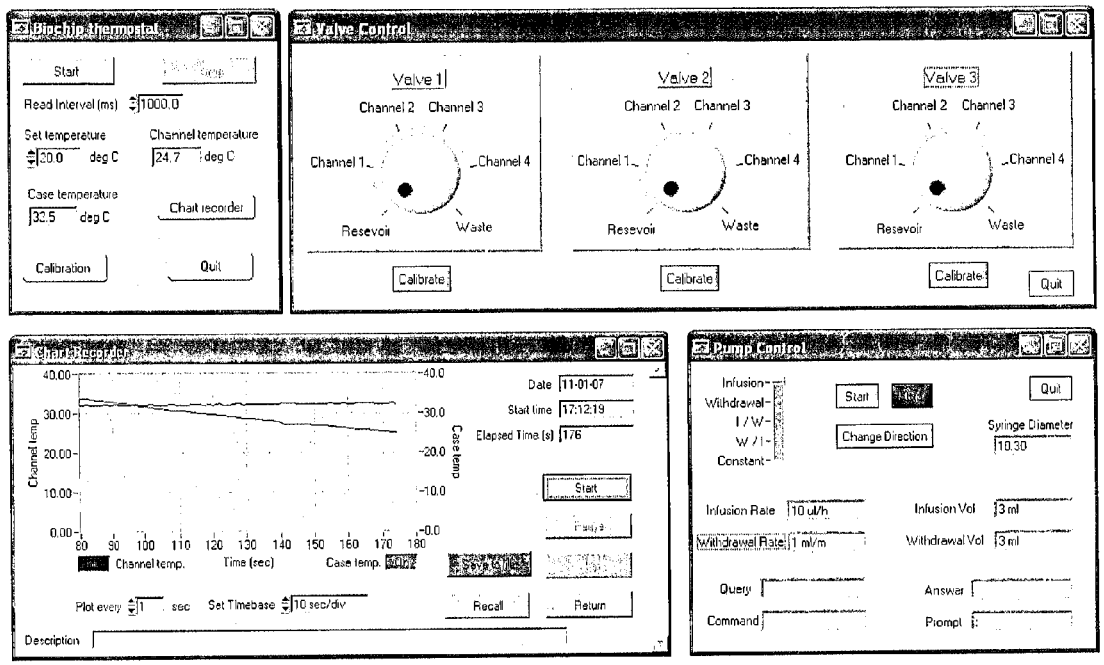
FIG. 15 shows an exemplary graphical user interface (GUI) for use with the apparatus of FIG. 14.

The apparatus of FIG. 14 may be controlled, for example, via a graphical user interface (GUI) installed on an appropriate computer, for example as seen in FIG. 15.

Figure 16:
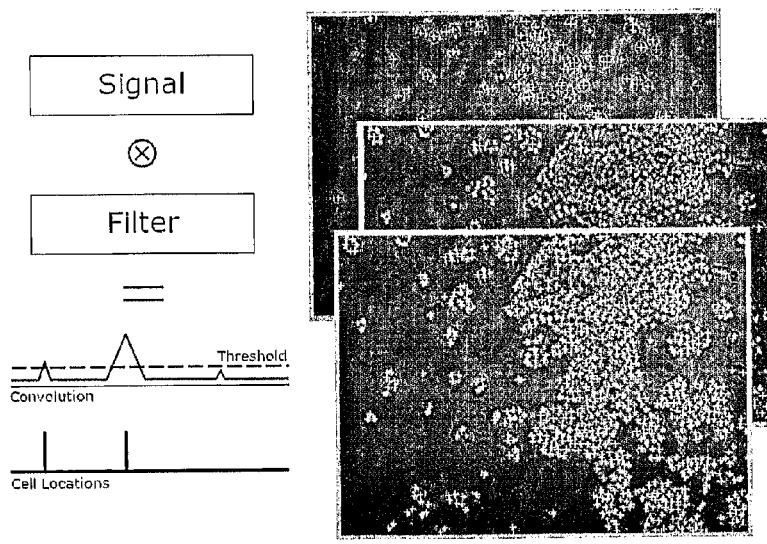
FIG. 16 illustrates, schematically, the signal processing technique used to detect the location of cells imaged by CyMap. The signal (see top of Fig.) from the detector is filtered and then a threshold is applied. Peaks in the filtered signal that exceed the threshold indicate cell locations ('line profiles')

FIG. 16 illustrates, schematically, use of the apparatus of FIG. 14 to detect cell locations. The signal (see top of Fig.) from the detector is filtered and then a threshold is applied. Peaks in the filtered signal that exceed the threshold indicate cell locations.

Figure 17:
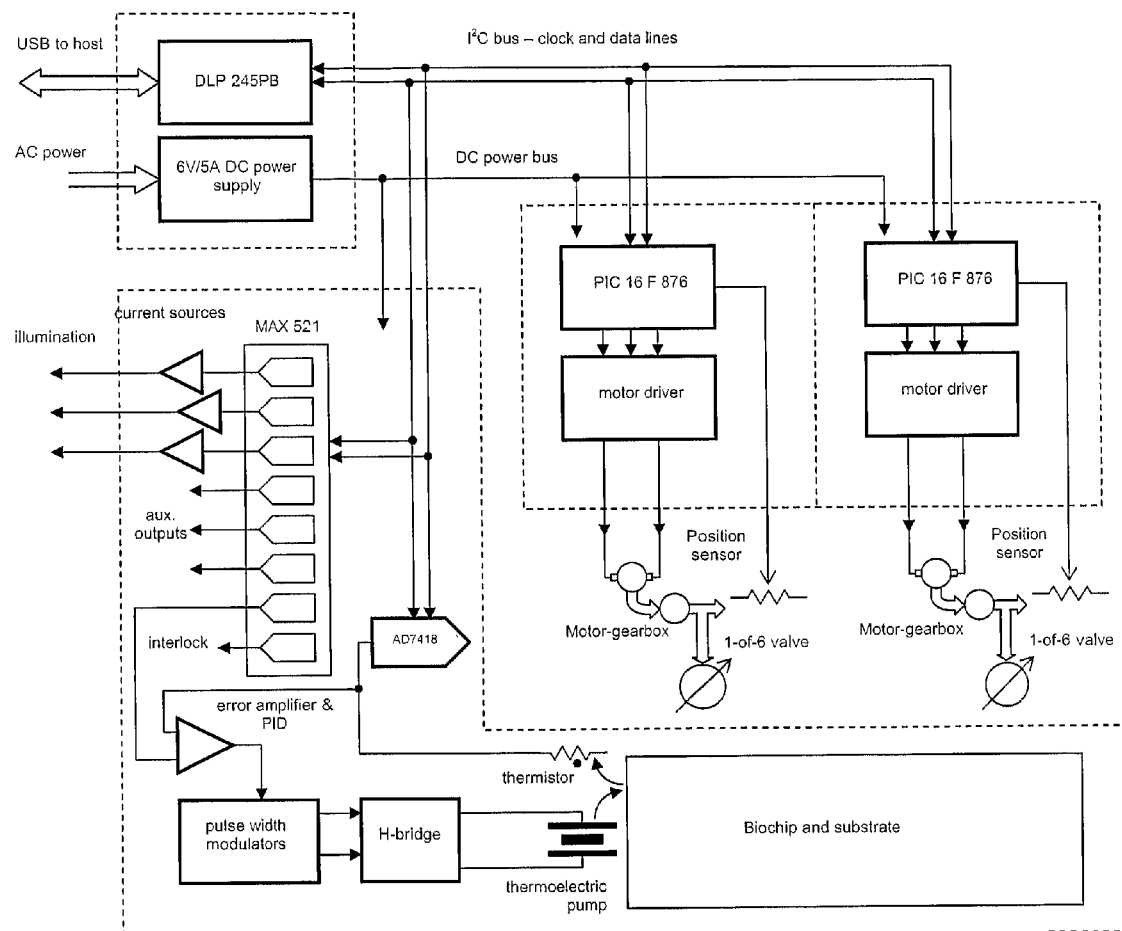
FIG. 17 shows another more detailed example of the possible control electronics for the apparatus of FIG. 14.

FIG. 17 shows another example of the possible control electronics for the apparatus of FIG. 14, incorporating temperature control of the cell environment using a thermoelectric pump. FIG. 17 also shows how a multiple channel digital-to-analogue converter can be used to provide control of light source intensities and temperature set-points.

Example 8

Cell Signatures

During a live cell assay, cells progressing towards mitosis (G2/M phase of the cell cycle) increase in size until just prior to cell division when they are approximately double their original size. This increase in diameter is accompanied by a change in shape during mitosis that alters the lensing properties of the cell. The combination of these two affects result in a discernibly different interference pattern for a cell in its G1 phase as compared to its G2/M phase.

Figure 23:
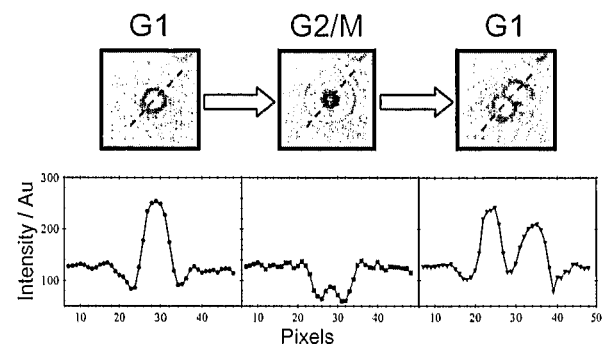
FIG. 23 illustrates the change in the diffraction patterns over a 30 minute period of a single osteosarcoma cell as it undergoes mitosis; Top—raw data, Bottom—Line profile taken through the raw data along the dashed line.

The experimentally recorded interference patterns for the human osteosarcoma cell line U-2 OS, with corresponding line profiles, produced at various stages of the cell cycle are presented in FIG. 23.

It is clear from the data that changes in the cells' interference patterns may be used as measures for inferring cellular events. Furthermore, changes in the morphology of cells during apoptosis may also be identified from the interference patterns.

Similarly this technique may be used to sort/distinguish different types of cells, which produce suitably different interference patterns, for example:
- Flat and round cells
- Cells with and without a nucleus (eg red and white blood cells)
- Large and small cells

Example 9

Cell Detection, Counting, Tracking and Locating

Under conventional microscopy, cells from the same cell line may appear very different in shape. One of the benefits of the CyMap imaging modality is that their interference patterns look very similar, since spatial information is stored within the fringes of the interference pattern. Thus objects/cells imaged in this manner can be readily detected and tracked through a combination of image processing algorithms [12] far more easily than if they were observed under conventional microscopy.

Figure 25:
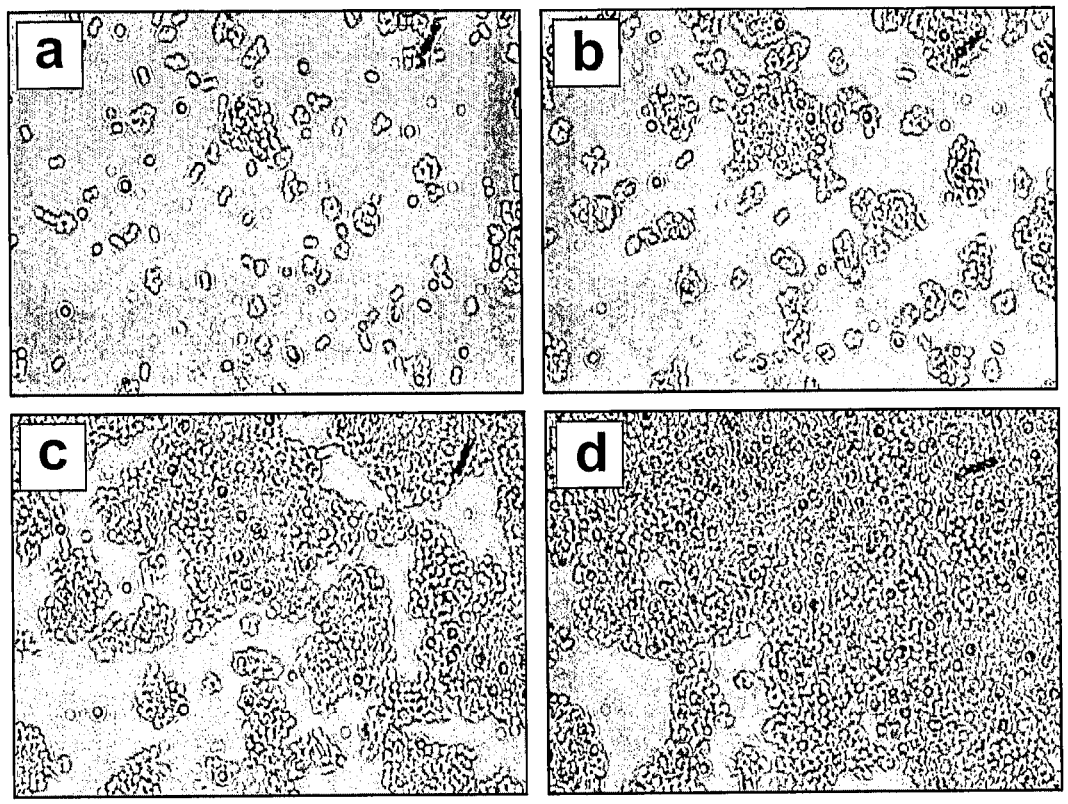
FIG. 25 shows time-lapse recordings of cell proliferation of U-2 OS cells, recorded using CyMap—the time interval between each of the sequential images (a, b, c, d) is 31 hours.

To demonstrate the capabilities of CyMap the proliferation of cells over time was recorded. The U-2 OS human osteosarcoma cell line was cultured in McCoy's 5A medium supplemented with 10% Fetal Calf Serum, 2 mM Glutamine, 100 u/ml Penicillin and 100 u/ml Streptomycin inside a conventional incubator with a humidified atmosphere of 5% $CO_2$, set at 37° C. Throughout the incubation period, the cells were monitored using the CyMap imaging system in time-lapse mode, with images recorded every 10 minutes. Four images from the sequence, each 31 hours apart, are presented in FIG. 25. Individual cells are clearly discernable as is colony formation, highlighting the suitability of CyMap for use in clonogenic and wound healing type assays.

Figure 24:
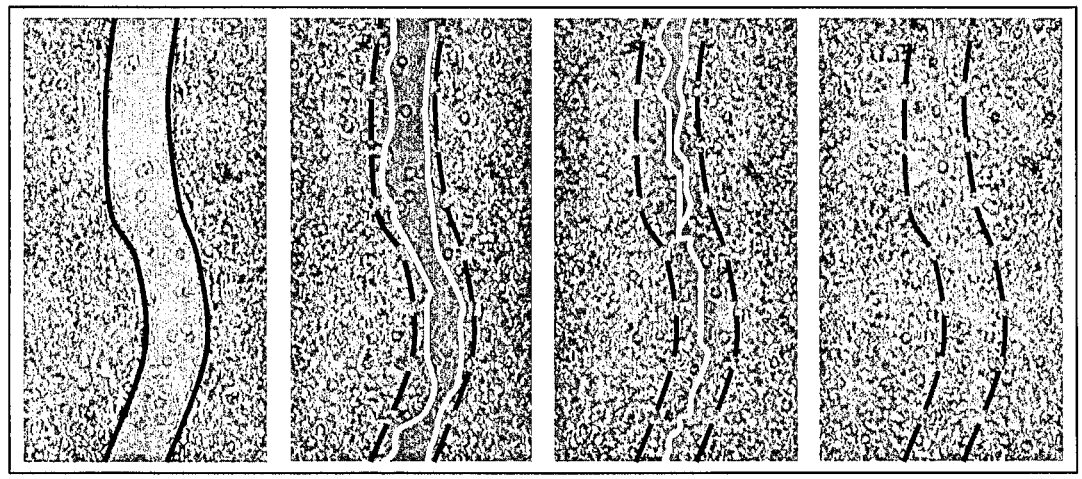
FIG. 24 shows a series of CyMap images demonstrating a wound healing assay—the dashed line denotes the original outline of the wound and the solid white line denotes the new wound outline.
Figure 26:
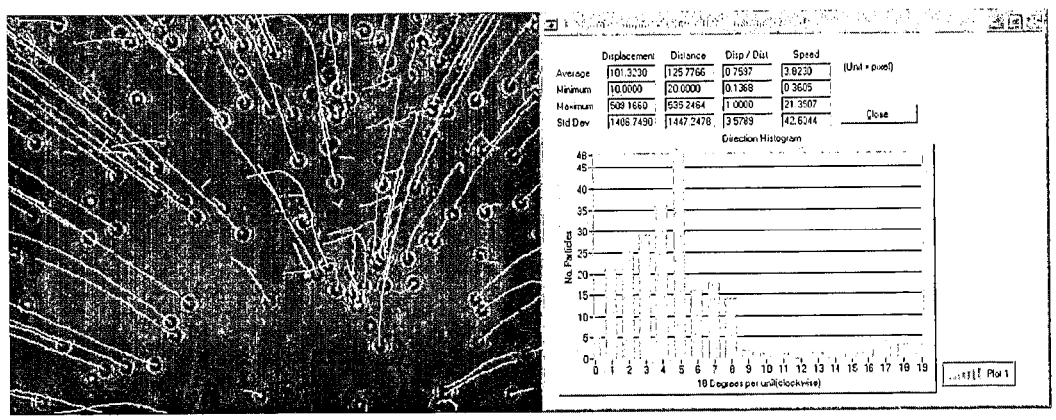
FIG. 26 shows, on the left-hand side a CyMap image showing the paths of tracked cells and on the right-hand side a panel show a histogram of the direction of cell movement for the tracked cells show in the CyMap image to the left.
Figure 27:
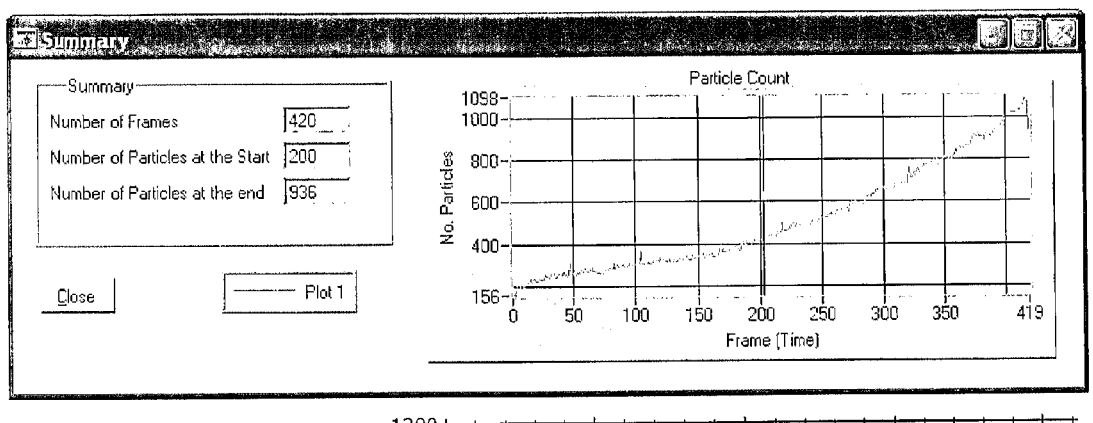
FIG. 27 shows in the panel at the top a display of the results from cell locating software showing the total number of cells per frame over a period of 419 frames and in the graph at the bottom the same data as in the panel plotted as a function of time—an exponential fit to the data has been applied; in this instance showing a cell doubling time of 28 hours.
Figure 27:
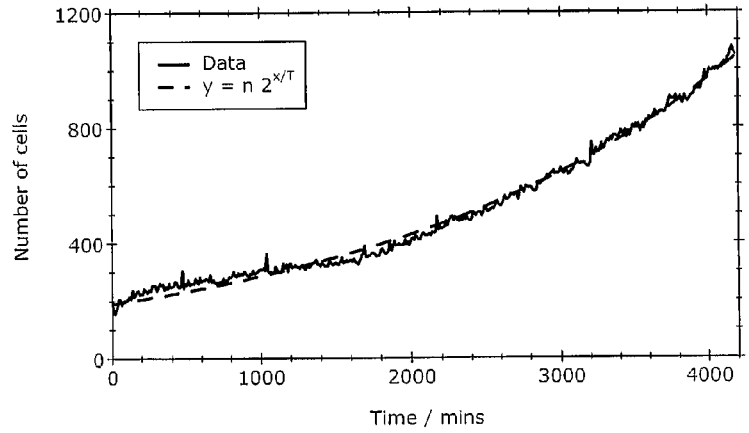

Therefore the combination of CyMap with post acquisition analysis makes assays that are traditionally difficult and time consuming easy to perform. Some examples that have been implemented on CyMap are:

Wound healing (FIG. 24 (and FIG. 6 discussed above in example 5))
Clonogenic Assays (FIG. 25)
Cell tracking—motility/chemotaxis assays (FIG. 26)
Determination of growth rates via cell counting (FIG. 27)

Figure 28:
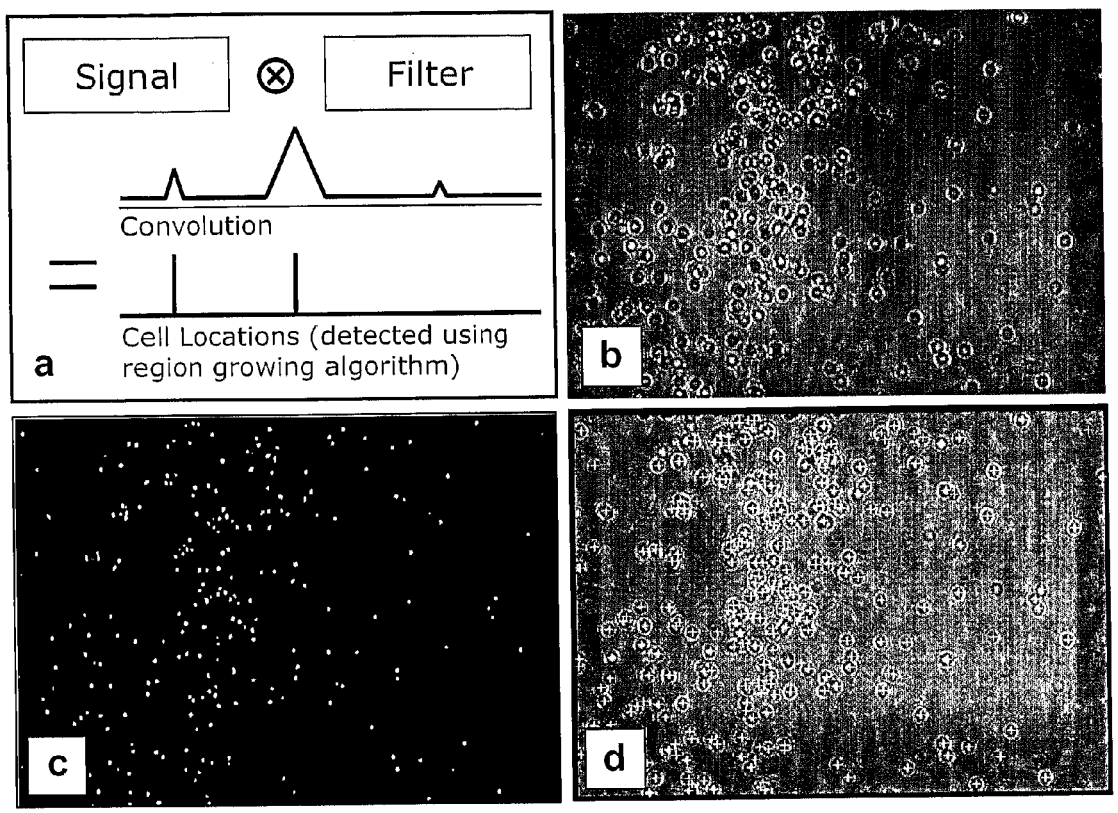
FIG. 28 illustrates a) a process used to detect cells; b) CyMap image of U-2 OS cells; c) response map; d) CyMap image with identified cells overlaid.

The inventors have shown that the signature arising from a cell can be robustly detected using a matched filter correlation technique because of its inter-cell consistency, in contrast to conventional microscopy. Correlation with a matched filter results in a response map that can be thresholded to obtain cell particles, as shown in FIG. 28c. The centre of mass of these particles indicates the centre of mass of a cell.

The matched filter can be chosen to identify the type of structure (signature) of interest, be it an attached cell, a rounded cell or a cell in mitosis. In tests against cell counts performed by human operators this automated method achieves up to 95% accuracy, but consistently achieves 80-90% accuracy.

Detecting cell numbers throughout a time-lapse sequence of images can then be performed in an automated manner. A consistent accuracy through a sequence is harder to achieve but the inventors have obtained an 80-90% accuracy. Different matched filters can be used to identify changes in cell state through a sequence.

Cell detections at individual frames can be linked to form continuous cell tracks that contain information about the cells motion and changes in state. FIG. 26 illustrates the results of tracking of single-state cells throughout a sequence as part of a chemotaxis assay using a model based approach. In this approach a model is held in the computer of every cell detected that contains information about the cell's position, velocity, acceleration and intensity profile at each frame in the sequence. In this way the correspondence between individual detections in different frames can be determined through prediction of a cell's motion via the model. The information derived from these tracks can be used to draw statistical conclusions about population movement; in order to achieve this, individual motions are calculated and thus also known.

In this example, U-2 OS cells were seeded onto four, two well chambers, 2 ml @ $2\times10^3$ cells per ml. One chamber was placed on CyMap and images were recorded every 10 mins for 2.7 days. The remaining chambers were placed alongside CyMap in the incubator.

After 24 hours one chamber was removed and the number of cells present counted using a Coulter counter, two readings from each well were, taken. The number of cells in the second chamber was counted after 48 hours and the final chamber after 72 hours, the data are given in the table below.

| Time/ | Chamber A | | Chamber B | | |
|---|---|---|---|---|---|
| hours | 1 | 2 | 1 | 2 | Average |
| 0 | $4 \times 10^3$ | | $4 \times 10^3$ | | $4 \times 10^3$ |
| 24 | $5.6 \times 10^3$ | $4.6 \times 10^3$ | $6.7 \times 10^3$ | $5.9 \times 10^3$ | $5.2 \times 10^3$ |
| 48 | $11.8 \times 10^3$ | $10.1 \times 10^3$ | $9.6 \times 10^3$ | $9.1 \times 10^3$ | $10.2 \times 10^3$ |
| 72 | $15.3 \times 10^3$ | $15.9 \times 10^3$ | $23.2 \times 10^3$ | $22.3 \times 10^3$ | $19.2 \times 10^3$ |

*Cell numbers are given per ml

Figure 29:
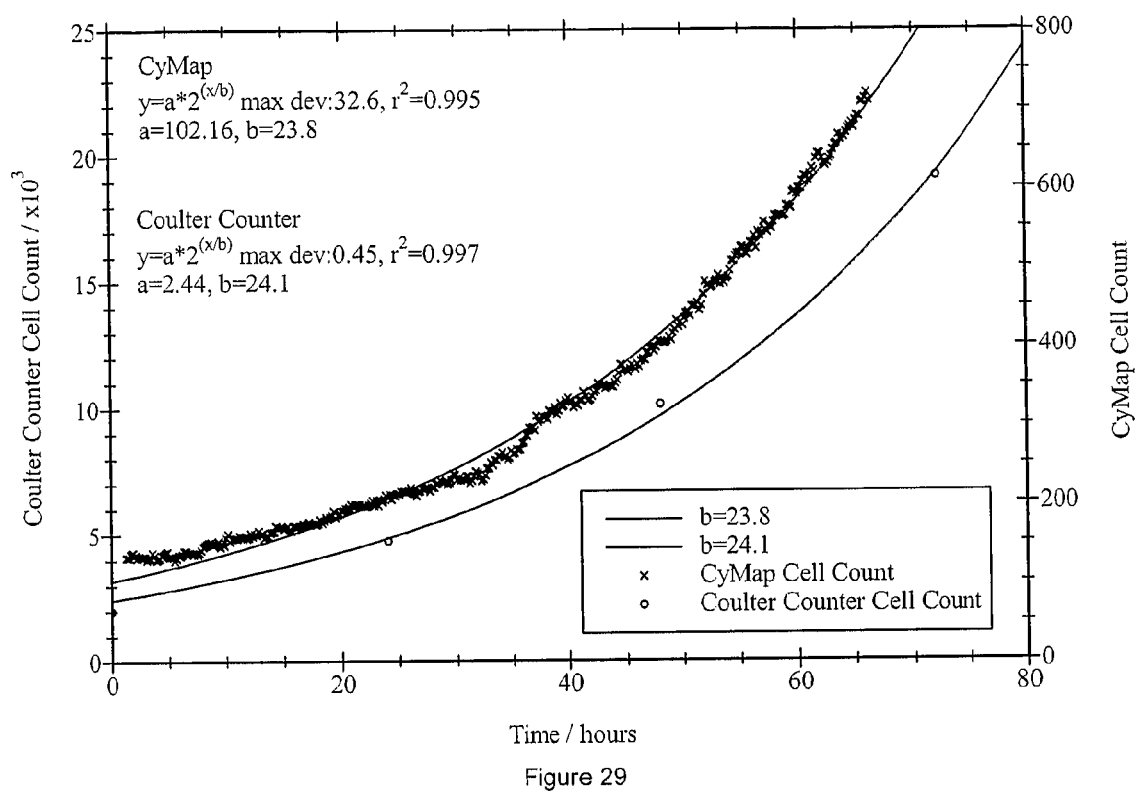
FIG. 29 is a graph showing U-2 OS growth rates as determined by CyMap (crosses) and a Coulter counter (circles)

The average Coulter counter values along with the CyMap count values are presented in FIG. 29.

The growth rate of a division every 23.8 hours is within 2% of the value determined by the Coulter counter. The advantage of using CyMap is that it illuminates any variations due to the need to use several different chambers in the Coulter counter method and you have a visual record of cell growth. This provides a useful check on cell confluency, which can ultimately modify the growth rate.

Further processing could be developed to detect changes in cell state such that mitosis events can be determined, e.g. by analysing the temporal signature in intensity and response to specific matched filters. Biologically-relevant parameters such as mitosis rates are then apparent. Furthermore, with full tracking and state change information, cell lineage and progeny studies could be performed.

The above discussion exemplifies automated: cell detection, counting, tracking, and trajectory analysis using the CyMap device.

Example 10

Incorporation into a Microfluidic System

Figure 30:
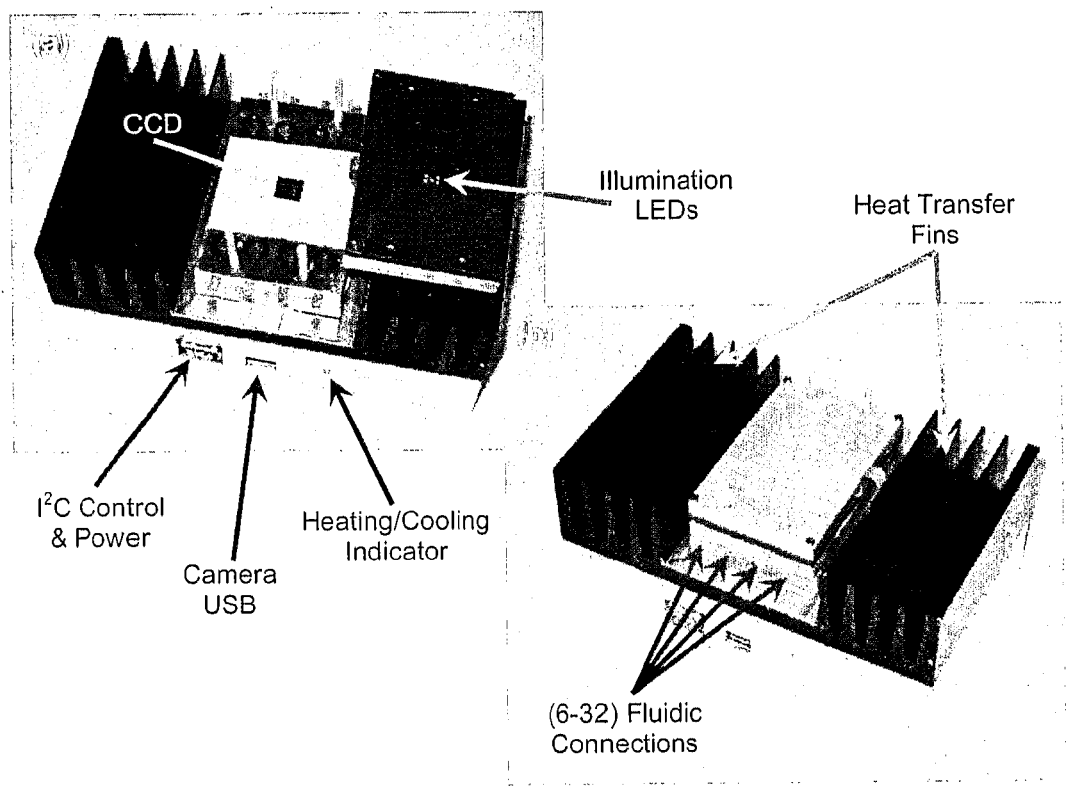
FIG. 30 shows photos of a microfluidic platform incorporating the CyMap imaging system. Photo (a) shows the 'lid' comprising the illuminating LEDs open and folded back onto the cooling fins, revealing the LEDs and the CCD. The microfluidics are normally placed between the LEDs and the CCD. Photo (b) shows the lid closed.

Due to its compact size the CyMap device is ideally suited as an imaging device in microfluidic systems. To demonstrate this the inventors have embedded the CyMap system in a microfluidic platform. Photographs of the microfluidic platform are shown in FIG. 30.

The capabilities of CyMap were also tested in a microfluidic environment. Poly(dimethylsiloxane) (PDMS) channels were fabricated by pouring PDMS (mixed in a 10:1 weight ratio) over a mould made using a dry film photoresist (Mega Electronics, UK). The PDMS was allowed to self-level, and then heated to a temperature of 70° C. for 1 hour to aid curing. The cured PDMS was then peeled off, treated with oxygen plasma (created using a Tesla coil) for 5 minutes, brought together with a glass slide and heated to 90° C. for 20 minutes to further strengthen the bond. Once cooled and incorporated into the CyMap microfluidic device, U-2 OS cells were injected through the PDMS into to the channels using a 23 gauge needle. The flow of the cells down the channel was recoded using CyMap in live imaging mode.

Figure 31:
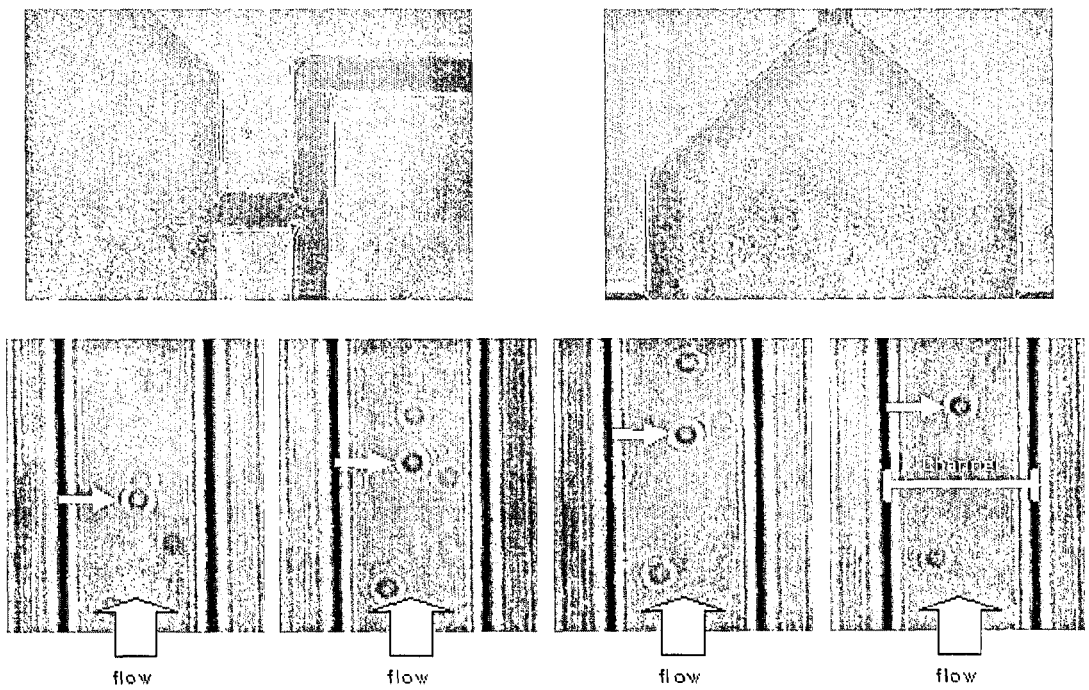
FIG. 31 shows: CyMap images of PDMS microfluidic channels (top) and a sequence of CyMap images showing cells travelling down a 500 μm wide PDMS fluidic channel (bottom).

A series of frames from the video sequence is shown in FIG. 31, along with images of the PDMS microfluidic channel. The dark lines in the images are caused by the walls of a 500 µm wide channel. The arrow in the frame sequence indicates the travel of one cell as it moves down the channel.

Once again this highlights CyMap's effectiveness for cell based LOC applications as well as demonstrating its suitability for monitoring chemotaxis assays.

Embodiments of the invention have been described above by way of example. Various modifications are possible without departing from the invention, for instance:

The integration of a miniature incubator around the device.
The integration of one or more CyMap devices into an incubator.
The use of IP video or "networked camera" for remote monitoring.
The use of wireless technologies for remote monitoring (e.g. Bluetooth, WiFi)
The use of microfluidics for automated perfusion.
The use of microfluidics for multiple chambers on-chip with addressable perfusion.
The use of microfluidics for the introduction and removal of cells from the imaging chamber or well.
The linking of two or more CyMap devices to enable the use of a single recording, processing and reporting station for multiple devices.
The use of light sources of different wavelengths (e.g. red, green and blue for colour imaging, or other wavelengths including UV for fluorescence excitation).
The use of fluorescence detection.
The use of the device for imaging fixed material (e.g. cellular or histological tissue sections).
The use of ambient light through a pinhole along with a light-shielded imaging path.

Furthermore, although embodiments of the invention have been discussed above with reference to the detecting, counting and tracking cells, embodiments of the invention can also be used to detect other objects/particles. For instance, the concepts discussed above can be used to detect bacteria, useful for monitoring water purity for example, or granules within fluids, which might be useful, for example, for detecting contaminants in the fluid or otherwise quality checking the fluid (e.g. in food quality control tests). Another potential application for the concepts discussed above is to monitor the capture on beads or cells on microfluidic chips for diagnostic applications, for instance the detection and/or capture of circulating tumour cells or pathogens and monitoring levels of certain antigens in blood/tissue samples by bead capture. The technology can also be used in miniature counting systems for these and other applications and is particularly suitable for hand-held devices (e.g. hand-held blood cell counters).

REFERENCES

Incorporated Herein by Reference

1. X. Cheng, Y. Liu, D. Irimia, U. Demirci, L. Yang, L. Zamir, W. R. Rodriguez, M. Toner and R. Bashir, *Lab Chip,* 2007. 2007(7): p. 746.
2. A. D. Elder, S. M. Matthews, J. Swartling, K. Yunus, J. H. Frank, C. M. Brennan, A. C. Fisher and C. F. Kaminski, *Opt. Express,* 2006. 14(12): p. 5456-5467.
3. D. R. Matthews, H. D. Summers, K. Njoh, R. J. Errington, P. J. Smith, P. Barber, S. Ameer-Beg and B. Vojnovic, *Appl. Optics,* 2006. 45(9): p. 2115-2123.
4. J. Emmelkamp, F. Wolbers, H. Andersson, R. S. DaCosta, B. C. Wilson, I. Vermes and A. van den Berg, *Electrophoresis,* 2004. 25(21-22): p. 3740-3745.
5. A. Daridon, M. Sequeira, G. Pennarun-Thomas, H. Dirac, J. P. Krog, P. Gravesen, J. Lichtenberg, D. Diamond, E. Verpoorte and N. F. de Rooij, *Sens. Actuator B-Chem.,* 2001. 76(1-3): p. 235-243.
6. X. Heng, D. Erickson, L. R. Baugh, Z. Yaqoob, P. W. Sternberg, D. Psaltis and C. H. Yang, *Lab Chip,* 2006. 6(10): p. 1274-1276.
7. D. Lange, C. W. Storment, C. A. Conley and G. T. A. Kovacs, *Sens. Actuator B-Chem.,* 2005. 107(2): p. 904-914.
8. Supplied by Dr D. Matthews and Dr H. Summers, School of Physics and Astronomy, Cardiff University.
9. J. Beuthan, O. Minet, J. Helfmann, M. Herrig and G. Muller, *Phys. Med. Biol.,* 1996. 41(3): p. 369-382.
10. C. L. Curl, C. J. Bellair, T. Harris, B. E. Allman, P. J. Harris, A. G. Stewart, A. Roberts, K. A. Nugent and L. M. D. Delbridge, *Cytom. Part A,* 2005. 65A(1): p. 88-92.
11. W. Z. Song, X. M. Zhang, A. Q. Liu, C. S. Lim, P. H. Yap and H. M. M. Hosseini, *Appl. Phys. Lett.,* 2006. 89(20).
12. C. Zimmer, B. Zhang, A. Dufour, A. Thebaud, S. Berlemont, V. Meas-Yedid and J. C. Olivo Marin, *IEEE Signal Process. Mag.,* 2006, 23(3): p. 54-62.
13. J. Garcia-Sucierquia W. Xu, S. K. Jericho and P. Klagges, M. H Jericho and H. Juergen Kreuzer *Digital in-line holographic microscopy* 2006, *Applied Optics,* vol. 45, 5, 636-850
14. H. Juergen Kreuzer Holographic microscope and method of hologram reconstruction. U.S. Pat. No. 6,411,406 B2 June 2002
15. H. Juergen Kreuzer and M. H Jericho Methods for tracking particles and life forms in three dimensions and in time. U.S. Pat. No. 6,876,474 B2 April 2005
16. P. E. Norgren of Perkin Elmer, 1969 *Annals of the New York Academy of Sciences.* 157, 514-524.
17. Francis T. S. Yu, *The Fresnel-Kirchoff Theory or Huygens' Principle,* The MIT Press, Cambridge, Mass., 1973, pp. 359-60, chapter. B (appendix).
18. Joseph W. Goodman, *Foundations of Scalar Diffraction Theory,* McGraw-Hill, San Francisco, 1968, pp. 34-7, chapter. 3.

The invention claimed is:

1. Apparatus for detecting objects in a sample, the apparatus comprising:
   an incoherent point light source;
   a detector having an active light detecting surface positioned and configured to detect diffraction or interference light patterns incident on the said surface, produced by light from the point light source which extends along a path which expands laterally outwardly from the point light source to said surface, along which path it interacts with objects in a sample;
   a sample holding location spaced from the said surface at which the sample is held in a sample holder or holders in the transmission path of light from the point light source to the said surface, the distance from the sample holding location to the said surface being less than the distance from the point light source to the sample holding location and allowing the light from the point light source, upon interacting with the objects in the sample to form said diffraction or interference light patterns at the said surface; and
   a processor configured to receive input from the detector indicative of the said diffraction or interference light patterns incident on the detector at the said surface, and processing said input to determine the presence of an object within the sample directly from the said incident diffraction or interference light patterns.

2. Apparatus according to claim 1, comprising a plurality of additional incoherent point light sources spaced from one another, light from each of the point light sources being incident on the detector subsequent to passing through the sample holding location, and wherein the apparatus further comprises a light source controller for controlling the point light sources such that not all of the point light sources emit light simultaneously.

3. Apparatus according to claim 2, wherein the light source controller controls the point light sources to emit light sequentially.

4. Apparatus according to claim 1, wherein at least one incoherent point light source is apertured to a diameter of no more than 100 μm.

5. Apparatus according to claim 1, wherein at least one incoherent point light source is a light emitting diode.

6. Apparatus according to claim 1, wherein at least one incoherent point light source is an optical fibre.

7. Apparatus according to claim 1, wherein the said surface is a pixelated array.

8. Apparatus according to claim 7, wherein the detector is a CCD or CMOS detector.

9. Apparatus according to claim 1, wherein the processor is arranged to determine the spatial location within the sample holding location of a detected object from the said input of the incident light patterns.

10. Apparatus according to claim 9, wherein the spatial location is determined in two dimensions in a plane parallel to the plane of said surface.

11. Apparatus according to claim 9, wherein the spatial location is determined in three dimensions.

12. Apparatus according to claim 3, wherein the processor is arranged to determine the spatial location in three dimensions within the sample holding area of a detected object from the said input of the incident light patterns.

13. Apparatus according to claim 1, wherein the detector is arranged to capture a series of two or more sequential light patterns over a period of time and the processor is arranged to analyze the series of light patterns to determine whether the location of a detected object at the sample holding location has changed.

14. Apparatus according to claim 13, wherein the processor is arranged to record a sequence of locations of an object within the sample holding location to determine the trajectory of the cell or bacterium.

15. Apparatus according to claim 1, wherein the detector is arranged to capture a series of two or more sequential light patterns over a period of time and the processor is arranged to analyze the series of light patterns to detect a change in the light pattern associated with a specific detected object, indicating a change in relation to a detected object other than a change in its location.

16. Apparatus according to claim 15, wherein the object is a cell and the change is cell attachment or cell mitosis or cell death.

17. Apparatus according to claim 1, wherein the processor is arranged to analyze the detected light patterns to count the number of detectable objects in the sample.

18. Apparatus according to claim 1, wherein the detected light is in the form of diffraction patterns.

19. Apparatus according to claim 1, wherein the detected light is in the form of interference patterns.

20. A microfluidic platform comprising apparatus for detecting objects according to claim 1.

21. Apparatus for detecting objects in a plurality of samples, the apparatus comprising a plurality of sample holders and a detecting apparatus according to claim 1.

22. Apparatus according to claim 21, wherein the plurality of sample holders are provided by a multi-well plate.

23. Apparatus according to claim 21, the detecting apparatus being movable relative to said plurality of sample holders to sequentially bring said sample holders into the sample holding location of the detecting apparatus.

24. Apparatus according to claim 21, comprising a plurality of said detecting apparatus, whereby a plurality of said sample holders can be located in respective sample holding location of the detecting apparatus simultaneously.

25. Apparatus according to claim 1, wherein said objects are cells or bacteria.

26. An apparatus according to claim 1, wherein the apparatus is a hand held device.

27. An apparatus according to claim 26, where the hand held device is a blood cell counter.

28. An apparatus according to claim 1, including a plurality of point light sources, each at a different wavelengths.

29. An apparatus according to claim 28, wherein the different light sources can be red, green or blue for color imaging.

30. An apparatus according to claim 28, where the different light sources can include ultra violet for fluorescence excitation.

31. An apparatus according to claim 1, wherein the processor is configured to derive features of the cells using signal processing methods.

32. An apparatus according to claim 1, wherein the detected light source is fluorescence.

* * * * *